US012653931B2

(12) United States Patent
Godin

(10) Patent No.: US 12,653,931 B2
(45) Date of Patent: Jun. 16, 2026

(54) METHODS AND DEVICES FOR MEDICAL IMPLANTS

(71) Applicant: BIOMEDIX, S.A., Geneva (CH)

(72) Inventor: Norman Godin, Geneva (CH)

(73) Assignee: BIOMEDIX S.A., Geneva (CH)

( * ) Notice: Subject to any disclaimer, the term of this patent is extended or adjusted under 35 U.S.C. 154(b) by 205 days.

(21) Appl. No.: 18/234,438

(22) Filed: Aug. 16, 2023

(65) Prior Publication Data

US 2024/0024541 A1 Jan. 25, 2024

Related U.S. Application Data

(63) Continuation of application No. PCT/US2022/070759, filed on Feb. 22, 2022.

(60) Provisional application No. 63/200,212, filed on Feb. 22, 2021.

(51) Int. Cl.
| | |
|---|---|
| *A61L 31/00* | (2006.01) |
| *A61F 5/00* | (2006.01) |
| *A61L 31/02* | (2006.01) |
| *A61L 31/08* | (2006.01) |
| *A61L 31/16* | (2006.01) |

(52) U.S. Cl.
CPC .......... *A61L 31/005* (2013.01); *A61F 5/0076* (2013.01); *A61L 31/022* (2013.01); *A61L 31/08* (2013.01); *A61L 31/16* (2013.01); *A61L 2300/30* (2013.01); *A61L 2300/64* (2013.01); *A61L 2430/22* (2013.01)

(58) Field of Classification Search
CPC ...... A61L 31/005; A61L 31/022; A61L 31/08; A61L 31/16; A61L 2300/30; A61L 2300/64; A61L 2430/22; A61F 5/0076; A61F 5/00; A61B 17/00
See application file for complete search history.

(56) References Cited

U.S. PATENT DOCUMENTS

| | | | | |
|---|---|---|---|---|
| 5,665,077 A | * | 9/1997 | Rosen ....................... | A61F 2/90 604/266 |
| 2003/0114921 A1 | | 6/2003 | Yoon | |

(Continued)

FOREIGN PATENT DOCUMENTS

| | | | | |
|---|---|---|---|---|
| JP | 2019-503819 A | 2/2019 | | |
| WO | WO-03086246 A1 | * 10/2003 | ........... | A61F 5/0089 |

(Continued)

OTHER PUBLICATIONS

"Regenerative Medicine Strategies for Esophageal Repair," Tissue Engineering: Part B, Londono et al., 2015 (Year: 2015).*

(Continued)

*Primary Examiner* — Susan S Su

(74) *Attorney, Agent, or Firm* — Mark T. Vogelbacker; Eckert Seamans Cherin & Mellott, LLC

(57) ABSTRACT

A method for maintaining a medical device in place in a lumen of a hollow organ of a patient for a period of months or years includes not using a metal or bioresorbable self-expandable stent. Optionally, a platelet rich plasma (PRP) solution can be applied to a stent to integrate the stent into an interior passageway of a patient. The stent can optionally be formed of a nitinol and inserted through a mouth of the patient. Sutures can be used to attach the stent to the interior passageway of the patient.

6 Claims, 20 Drawing Sheets

(56)           References Cited

U.S. PATENT DOCUMENTS

| | | | |
|---|---|---|---|
| 2004/0071786 A1* | 4/2004 | Grippi | A61L 24/106 |
| | | | 424/530 |
| 2010/0256775 A1 | 10/2010 | Belhe | |
| 2011/0015720 A1* | 1/2011 | Schnell | A61L 31/022 |
| | | | 604/288.03 |
| 2013/0231733 A1 | 9/2013 | Knisley | |
| 2014/0276336 A1 | 9/2014 | Sharma | |
| 2015/0366653 A1 | 12/2015 | Noishiki | |
| 2018/0360626 A1 | 12/2018 | Yaniv | |

FOREIGN PATENT DOCUMENTS

| | | | | |
|---|---|---|---|---|
| WO | WO-2017132676 A1 * | 8/2017 | | A61F 5/00 |
| WO | WO-2019155284 A1 * | 8/2019 | | A61F 5/0073 |

OTHER PUBLICATIONS

"Endoscopic Submucosal Dissection," Cleveland Clinic (Year: 2023).*
Written Opinion of International Patent Application No. PCT/US2022/070759 Dated Jun. 3, 2022.

* cited by examiner

METHODS AND DEVICES FOR MEDICAL IMPLANTS

CROSS-REFERENCE TO RELATED APPLICATION

The present application is a continuation application of International Patent Application No. PCT/US2022/070759, filed on Feb. 22, 2022, entitled "METHODS AND DEVICES FOR MEDICAL IMPLANTS", which claims priority to U.S. Provisional Application No. 63/200,212, filed Feb. 22, 2021 and titled "METHODS AND DEVICES FOR LONG-TERM ESO-GASTRO-INTENSTINAL IMPLANTS," the disclosure of each is hereby incorporated by reference.

FIELD

The presently disclosed technology relates generally to medical devices, prosthesis, and methods of using and/or implanting same. More particularly, one embodiment of the presently disclosed technology relates to methods and devices to place long-term implants in the wall and/or lumen of the esophagus of a patient to treat any of a variety of ailments, including but not limited to gastro-esophageal reflux disease and/or obesity, often without surgery.

BACKGROUND

Obesity, for example, affects up to 40% of the world population. Removal of portions of the stomach and gastric by-pass are known treatments that are invasive and challenging procedures. Developing safe and relatively non-invasive methods of treatment could have an important impact on large segments of the population.

Further, reflux is an ailment that also affects a large portion of the world population. It is known to use a prosthesis to treat Gastro-Esophageal Reflux Disease (GERD) and/or to help a patient reduce their weight. Examples of such prior art devices are disclosed in WO 2019/155284, WO 2018/222819, and WO 2013/050381, which are hereby incorporated by reference.

Despite benefits, existing methods and devices used to treat reflux and/or obesity have drawbacks. For example, in WO 2019/155284, the mesh ring is not attached to the helical spring ring with sutures and the device tends to fall into the stomach before it can be integrated into the wall. In WO 2018/222819, food cannot pass between the wall of the esophagus and the device with a thicker ring since the mesh ring supporting the device is within the wall of the esophagus.

BRIEF SUMMARY

While the prior art systems are beneficial in numerous ways, the systems, methods and devices of the presently disclosed technology provide benefits over what is currently known in the art.

In one embodiment, the presently disclosed technology provides a method of allowing integration of the mesh ring using platelet rich plasma (PRP) obtained from the patient's own blood and the mesh ring is integrated within the wall of the esophagus between the PRP added to the biopsy sites of the wall of the esophagus, which helps coagulation and "grips" the mesh on the external side of the mesh and esophageal cell wall stem cells that are obtained from the biopsies and are "recycled" and reinjected on the "internal" or luminal side of the mesh ring.

The most common reason for treatment of lesions of the esophagus is GERD. GERD is almost always treated with Proton Pump Inhibitors and/or antacids that block acid production so that the reflux is much less or not acidic anymore and the esophageal lesions heal. Prior to the presently disclosed technology, no one has bothered using PRP, as the cause of acid reflux, namely acid production, is not stopped and the esophageal lesions would recur very fast, the heartburn symptoms will not improve so there has been no good reason to use PRP in the esophagus until now. PRP and esophageal adult stem cells will help obtain a better integration of the mesh in the wall of the esophagus and the third and last ring (after the first ring compressing the wall of the esophagus or DM-1 (Diagnosis and Management 1) and the DM-2 (Therapeutic mesh ring), the DM-3 ring puts pressure on the area to help integrate the mesh supporting the tubular devices treating GERD and obesity in the wall of the esophagus.

All of this is done at standard endoscopy through the mouth, so no open or laparoscopic surgery.

In one optional embodiment, the presently disclosed technology is directed to a device and method used to implant a variety of Gastro-intestinal Anti-Reflux Devices (GARD™) placed minimally-invasively or non-invasively through the mouth of the patient to treat gastro-esophageal reflux disease and obesity with autologous biological compounds.

BRIEF DESCRIPTION OF THE DRAWINGS

The foregoing summary, as well as the following detailed description of the presently disclosed technology, will be better understood when read in conjunction with the appended drawings, wherein like numerals designate like elements throughout. For the purpose of illustrating the presently disclosed technology, there are shown in the drawings various illustrative embodiments. It should be understood, however, that the presently disclosed technology is not limited to the precise arrangements and instrumentalities shown. In the drawings:

FIG. 2A illustrates a tubular-type GARD™ for GERD;

FIG. 2B illustrates a lamellar-type GARD™ for GERD;

DETAILED DESCRIPTION

Figure 1:
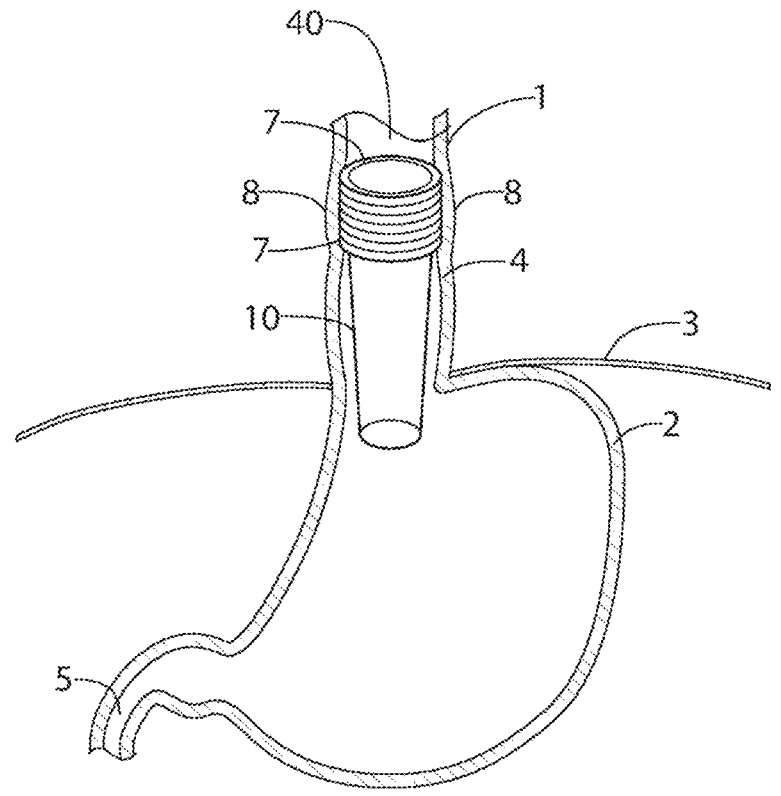
FIG. 1 illustrates a Diagnosis and Management (DM) GARD™ according to one embodiment of the presently disclosed technology.

While systems, devices and methods are described herein by way of examples and embodiments, those skilled in the art recognize that the presently disclosed technology is not limited to the embodiments or drawings described. Rather, the presently disclosed technology covers all modifications, equivalents and alternatives falling within the spirit and scope of the appended claims. Features of any one embodiment disclosed herein can be omitted or incorporated into another embodiment.

Any headings used herein are for organizational purposes only and are not meant to limit the scope of the description or the claims. As used herein, the words "may" and "can" are used in a permissive sense (i.e., meaning having the potential to or optionally) rather than the mandatory sense (i.e., meaning must). Unless specifically set forth herein, the terms "a," "an" and "the" are not limited to one element but instead should be read as meaning "at least one." The terminology includes the words noted above, derivatives thereof and words of similar import.

The method according to one embodiment of the presently disclosed technology includes GARDs™ placed through the mouth of a patient after calibration of the diameter of the patient's esophagus to select appropriately sized devices with a new Therapeutic Endoscopy technique to which autologous biological compounds are added, called a Therapeutic BIO-Endoscopy (TBE) procedure.

In one embodiment, first a DM GARD™ is placed to evaluate tolerance and efficacy but also to create a circular pressure niche in the esophageal wall of the patient. The DM GARD™ is then removed from the esophageal wall of the patient. Once the DM GARD™ is removed, the Therapeutic GARD™ device can be placed in the esophageal wall of the patient.

Therapeutic GARDs™ (e.g., the GARD™ for GERD and Obesity devices) are optionally made of 2 parts: a ring made out of a circular soft mesh in one embodiment or a stent, made out of metal or an alloy material like nitinol in another embodiment, and a tubular part. Collectively, the two parts comprise a structure sometimes referred to herein as a "prosthesis."

In one embodiment, the stent is a woven, knitted, or braided mesh structure, optionally in the form of a cylinder. The stent can be made from any of a variety of materials, such as stainless steel, nitinol (nickel titanium), or chrome-cobalt alloy, for example. In one embodiment, the stent can be formed of any material that provides super elastic capacity for folding to pass the stent through the mouth of the patient and its elasticity when released to expand and reach the niche when the stent is released.

In one embodiment, the mesh ring is placed within the wall of the esophagus after localized resection of the esophageal wall using a series of biopsies or deeper resection with Endoscopic Mucosal Resection (EMR) or Endoscopic Submucosal Dissection (ESD). The resection causes bleeding and plasma or PRP prepared from the patient's blood is injected or sprayed (e.g., through a catheter) to speed up coagulation and healing. Gluconate calcium can optionally be added to the PRP so that the solution is more viscous and helps adhere better to the bleeding niche.

The mesh ring of the Therapeutic GARD™ is then pressed mechanically with either a balloon mounted on the introduction delivery system that presses the mesh ring on the coagulating mix of blood and PRP/calcium gluconate or a self-deploying helical spring ring on which the mesh ring supporting the tube is mounted.

In the balloon embodiment, the balloon is then slowly deflated and removed or the knots holding the mesh ring to the helical spring are cut or pulled out if slip knots have been used and the ring is delicately pulled back in the esophagus or out of the body through the mouth leaving the mesh ring in place.

The patient's epithelial stems cells and possibly fibroblasts are optionally removed with the biopsies taken during placement of the DM GARD™ and put in culture in a laboratory. Or, the stem cells can be obtained when the biopsies (or EMR/ESD) are taken from the niche at the beginning of the therapeutic procedure are then placed in a PRP/calcium gluconate solution and are sprayed on the mesh ring on the luminal side of the mesh that supports the tubular devices. This is done to help reconstitute the epithelial layers of cells removed previously at resection. A balloon on the delivery catheter is inflated and presses the epithelial stem cells in PRP on the mesh and/or a third ring is placed at the end of the procedure to exert pressure for a longer period of time than an inflated balloon place through the mouth can.

In one embodiment, the mesh ring is integrated in the wall of the esophagus between the esophageal wall side (external) where the bottom of the niche and the coagulating blood with PRP/calcium gluconate mix is located and the luminal side (internal) that is reconstituted with the patient's own epithelial stems cells from the biopsies added to the PRP/calcium gluconate solution. In this way, the surgical mesh is "sandwiched" in the reconstituted wall.

The surgical mesh can be made of several different non-resorbable compounds, such as but not limited to polypropylene, polyester, polyethylene terephthalate (PET), polytetrafluoroethylene (PTFE), polyvinylidene fluoride (PVDF) among others that are all used safely for many years in surgery as well as some mesh that include animal collagen, and mixtures thereof. A ring is added in the lumen of the esophagus at the end of the procedure to help put pressure and help heal the esophageal wall now holding the mesh ring supporting the Therapeutic GARD™ in the gastro-intestinal lumen.

This new approach to Therapeutic Endoscopy is called Therapeutic Bio-Endoscopy (TBE) as a biological component is added, namely the autologous cells of the esophageal wall that have been resected and then reinjected to reconstitute the esophageal wall after the mesh of the devices supporting all the devices has been placed in the esophageal wall in the patient's platelet rich plasma (PRP), which is known to help heal lesions in other areas of medicine or dentistry. When only fragments of the esophageal biopsies containing stem cells (that have not been previously placed in cell culture in the laboratory) are used with a PRP/calcium gluconate solution, a localized "in vivo" culture milieu to reconstitute the esophageal wall is created. Other tissues (e.g., bone, tendon, cartilage, skin, hair, etc. . . . ) have been regenerated using PRP and appropriate stem cells.

See (1) Yamada Y, Ueda M, Naiki Tet al., Autogenous injectable bone for regeneration with mesenchymal stem cells and platelet-rich plasma: tissue-engineered bone regeneration. Tissue Eng. 2004 May-June; 10(5-6): 955-64. (2) Zhu M, Kong D, Tian R et al., Platelet sonicates activate hair follicle stem cells and mediate hair follicle regeneration, J Cell Mol Med. 2020 January; 24(2): 1786-1794. (3) Paoloni, J. et al., Platelet-rich plasma treatment for ligament and tendon injuries, Clin J Sport Med. 2011 January: 21(1): 37-45. (4) Etulain J. Platelets in wound healing and regenerative medicine. Platelets 2018 September; 29(6): 556-568. The disclosure of each of these references is incorporated by reference.

Table 1 below shows a summary of the GARD™ family of devices with the temporary DM-GARD™ placed first then removed and the Therapeutic-GARD™ separated in 2 families, the GARD™ device for GERD models and the Obesity GARD™ models for obesity.

TABLE 1

| Family of GARD ™ of devices 6 models of GARDs ™ divided in 3 groups. |
|---|

| I. | Diagnosis and Management (DM) GARD ™ (short term implant) |
| | Group 1. The DM-GARD ™ (1 model with several sizes of rings) |
| II. | Therapeutic GARDS ™ (long term implants) |
| | Group 2. GARD ™ for GERD. (2 models with several sizes of rings) The lamellar GARD ™ for GERD for mild to moderate GARD. The tubular GARD ™ for GERD for moderate to severe GERD. |
| | Group 3. The OBESITY GARDs ™ (3 models with several sizes of rings) OB1-GARD ™, obesity Class 1 (BMI 30 to 34.9) The GARD tubes reaches the stomach. OB2-GARD ™, obesity Class 2 (BMI 35 to 39.9) The GARD tube reaches the duodenum OB3-GARD ™, obesity Class 3 (BMI more than 40) The GARD tube reaches the jejunum |

Figures 3A, 3B, 3C:
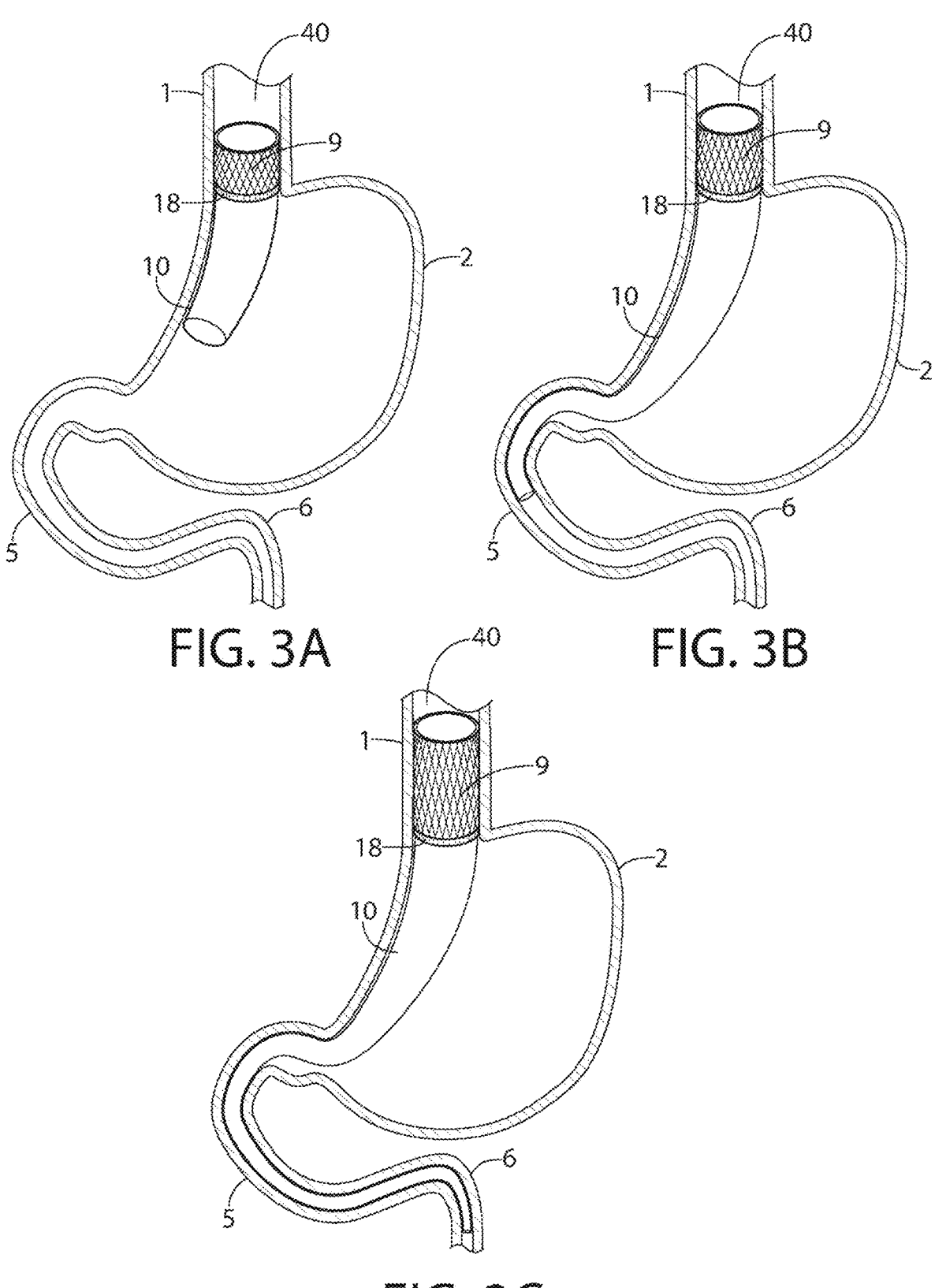
FIG. 3A illustrates one type of Obesity GARD™ according to one embodiment of the presently disclosed technology.
FIG. 3B illustrates another type of Obesity GARD™ according to one embodiment of the presently disclosed technology.
FIG. 3C illustrates yet another type of Obesity GARD™ according to one embodiment of the presently disclosed technology.

Various techniques are helpful to hold anti-reflux devices and anti-obesity devices in the lower esophagus of the living organism or patient. For example, the patient's adult stem cells can be "cultured" in vivo in the patient's own PRP obtained from the patient's blood. Another technique is to culture biopsies from the esophagus in an existing device made for cell culture/sorters in a lab. Using only components that can be reinjected in animals without immortalized cells, it is possible to culture their esophageal stem cells and demonstrate that in addition or instead of using in vivo cultures, one can use in vitro cultures in the lab taken from the animal, cultured and the cells that have multiplied can be used to recreate and/or repair an esophageal epithelium and thereby covering the nitinol stent holding the tubular devices for GERD (lamellar or tubular) and longer tubular devices as needed for the obesity GARDs™ (OB-1, OB-2 and OB-3), as shown in FIG. 3A-3C.

It is known to place staples at flexible endoscopy and perforate the wall of the esophagus to hold the GARD™ in place. One problem is that the staples can cause small holes through the different layers of the esophageal wall and secretions, often acid, passed from the lumen of the esophagus into the thorax and can cause mediastinitis in pigs.

Now, with the major development of laparoscopic surgery and even more with robotic surgery, it is possible to use laparoscopic technology to place a few sutures that have a greater range of motion and precision to place the sutures (2 to 10, preferably 3 to 5 sutures) using classical surgical curved needles through the abdomen than the classical laparoscopic techniques and give a better vision of the lower esophagus. When fluoroscopy is used additionally, it is easy for the healthcare professional to place his/her suture through the esophagus and through a nitinol stent, for example, to attach the stent securely to the wall of the esophagus. To avoid perforation as seen with metallic (e.g., nitinol) staples, the lumenal side as mentioned earlier can be covered with stem cells in PRP or provided by in vitro cultures as described earlier.

For the peritoneal/mediastinal sides of the sutures and the knot which the healthcare professional sees through the robot, a fibrin glue or fibrin sealant can seal the passage of the surgical thread through the wall of the esophagus as well as the knot tied by the healthcare professional on the "external" or peritoneal/mediastinal side) of the esophagus.

These techniques should prevent leakages and mediastinitis and/or peritonitis caused by placing sutures precisely under visual and X-ray control to suture the ring of the nitinol stent within the wall of the esophagus into the lumenal side. Benefits are also seen by placing the sutures from the laparoscopic side as well as using methods to "close" any "holes" caused by the passage of the surgical threads through the wall of the esophagus on the internal and external side, namely stem cells with PRP inside (lumen) and Tisseel (fibrin sealant) outside. A double approach can be employed, from inside the esophagus with endoscopy and outside the esophagus with laparoscopic surgery, preferably with a robot.

Another important method is to use the Apollo Endostitch device that allows a healthcare professional to do sutures through the mouth with a flexible endoscope and more recently with the Sx model using a classical one working channel endoscope, which most endoscopists use (instead of a 2 working channel endoscope that only very few endoscopists have as previously). It is now possible to secure the nitinol stent of the GARD™ in the wall of the esophagus using sutures placed through the mouth during placement of the Therapeutic GARD™ using the Apollo Endostitch Sx. This technique is beneficial as it can be done without surgery, through the mouth, on outpatients.

Referring now to the drawings in detail, wherein like numerals indicate like elements throughout, FIG. 1 illustrates the DM GARD™ placed in the esophagus (1) and the tubular (e.g., cylindrical and/or conical) part (10) reaching or extending into the stomach (2). The tubular part (10) is optionally flexible. Here, a hiatus hernia (4) often associated with moderate to severe GERD is shown. The diaphragm (3) separates the abdominal cavity underneath from the thorax above. The DM GARD'''s thick ring (7) holds in the esophagus mainly through pressure on the esophageal wall and makes the esophageal wall bulge creating a "niche" (8) that will be used to place the long-term Therapeutic GARD™ after the DM GARD™ has been removed. FIG. 1 also shows the lumen (40) of the esophagus.

Figure 2C:
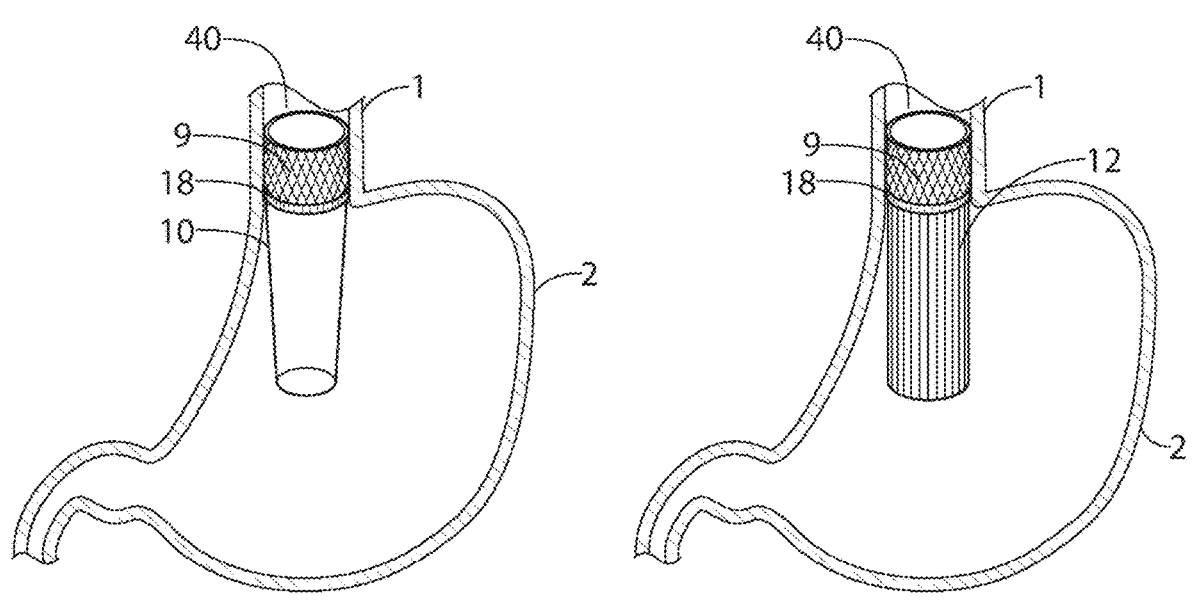
FIG. 2C illustrates another lamellar-type GARD™ for GERD.
Figure 2C:
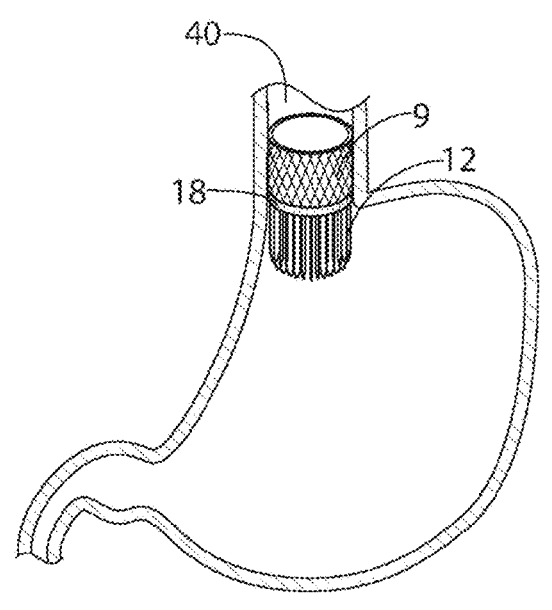

FIGS. 2A-2C illustrate the 2 main models used to treat GERD, namely in FIG. 2A, the GARD™ GERD device that blocks reflux and can also help patients who are overweight lose a few pounds. The GARD™ for GERD device blocks vomiting as surgery for reflux with its most common operation called the Nissen fundoplication also does. In FIG. 2B, the lamellar model (12) will also block reflux and allow vomiting when the lamellae under vomiting pressure turn back on themselves (FIG. 2C), but will have less effect on weight loss. An important feature is the radio-opaque zone (18) placed or located between the thinner mesh ring (9) and the tube (10) or the lamellae (12). This radio-opaque zone (18) will help locate the devices with fluoroscopy in case of need without having to do an endoscopy. FIGS. 2A-2C also show the lumen (40) of the esophagus. Optionally, the mesh ring (9) can be molded in silicone.

FIGS. 3A-3C illustrate 3 models of the Obesity GARD™. FIG. 3A shows the OB1-GARD™. FIG. 3B show the OB2GARD™. FIG. 3C show the OB3GARD™.

In FIG. 3A, the tube (10) of OB1GARD™ device ends in, terminates in, and/or extends into the stomach and can be used for people having class 1 obesity, which is a Body Mass Index (BMI) of 30 to 34.9. In this device, the effect is mainly restriction to help lose weight, which means that people will have to eat smaller quantities and chew their food longer.

In FIG. 3B, the tube (10) of the device reaches the duodenum (5) so the device will cross or pass the whole stomach entering the stomach (2) where the lower esophagus (1) meets the stomach (2) and ending in the duodenum (5). This device mimics the effect of the "sleeve gastrectomy" where the healthcare professional cuts % of the stomach on the greater curvature side leaving a narrow band along the lesser curvature now occupied by the tube (10). Of course, with the OB2-GARD™, the whole stomach is spared and % of the stomach are not removed. The OB2-GARD™ can be used for patients who have class 2 obesity with a BMI of 35 to 39.9. Note that the mesh ring supporting the tube will have to be implanted over a higher surface of the esophageal mucosa and certainly deeper than for the GARD™ for GERD devices or the OB1 devices.

For morbid obesity or patients having BMIs of over 40, the OB3-GARD™ (FIG. 3C) can be placed with the tube ending in the jejunum (6). As in the surgical gastric by-pass, the OB3-GARD™ will help lose weight both by restriction as for the OB2-GARD™ but also by creating malabsorption as food will stay in the tube and will not be in contact with enzymes from the pancreas, or duodenum nor with bile before reaching the duodenum, in many ways similarly to the effect of gastric by-pass but again without surgery and surgical risk as the mortality of gastric by-pass is estimated to be about 1% because these patients are obviously high risk patients because of their morbid obesity. Again, the mesh ring supporting the OB3GARD™ tube with have to cover a larger surface in the lower third of the esophagus and placed deeper in the esophageal wall. FIGS. 3A-3C also show the lumen (40) of the esophagus.

Table 2 below describes one method to obtain PRP from the patient's venous blood by centrifuging the blood twice. Other commercial centrifuges exist that allow for a single centrifugation, but usually the platelet concentration is lower than in this method and is therefore not recommended unless proven equivalent in platelet concentration.

TABLE 2

Platelet Rich Plasma Preparation.

1. Obtain whole blood by venipuncture in acid citrate dextrose (ACD) tubes.
2. Do not chill the blood at any time before or during platelet separation.
3. Centrifuge the blood using a 'soft' spin.
4. Transfer the supernatant plasma containing platelets into another sterile tube (without anticoagulant).
5. Centrifuge tube at a higher speed (a hard spin) to obtain a platelet concentrate.
6. The lower $\frac{1}{3}^{rd}$ is platelet rich plasma (PRP) and upper $\frac{2}{3}^{rd}$ is platelet-poor plasma (PPP). At the bottom of the tube, platelet pellets are formed.
7. Remove PPP and suspend the platelet pellets in a small quantity of plasma (e.g., 2-4 mL) by gently shaking the tube.
8. Add 3% to 5% gluconate calcium to make the preparation viscous.

Figure 4A:
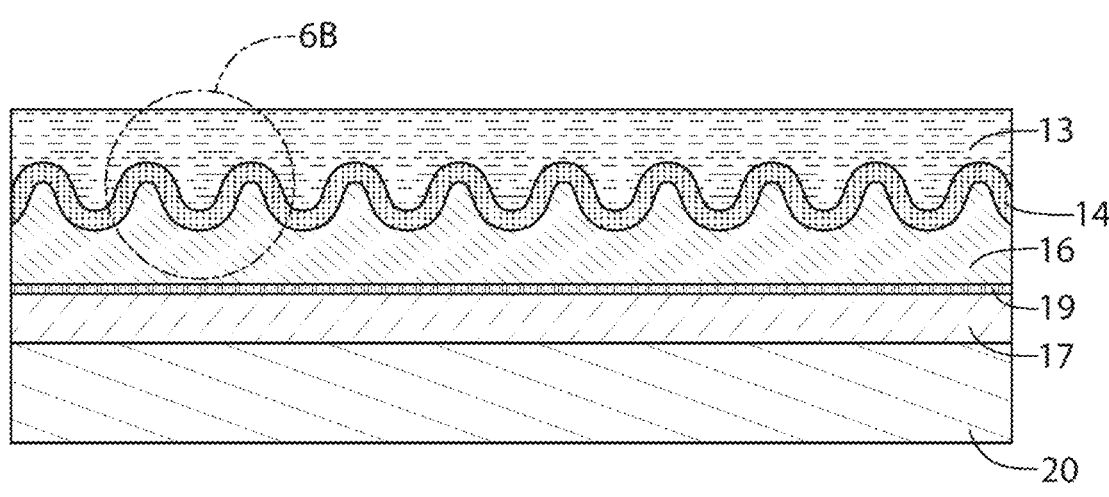
FIG. 4A illustrates normal layers of the esophageal wall of a human being.

FIG. 4A illustrates schematically the different layers of the normal human esophageal wall. If one considers that the esophagus is a tube, the innermost layer in contact with food ingested through the mouth and passing through the esophagus into the stomach is the esophageal epithelium (13) and the outer most layer is a muscular layer that will "push" the food down into the stomach from the mouth using a progressive wave of contraction called the peristaltic wave (20).

Figure 4B:
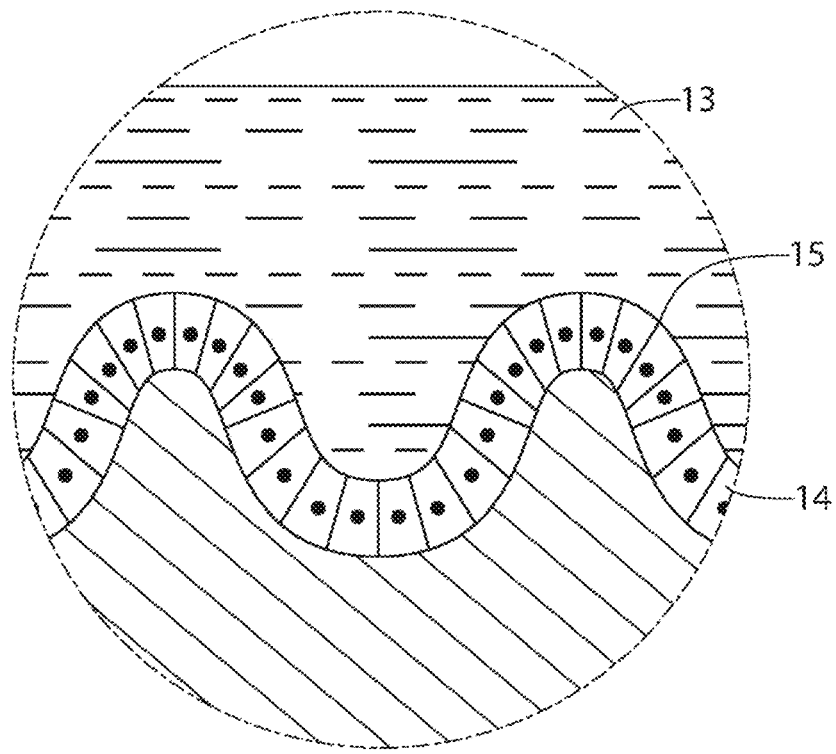
FIG. 4B illustrates adult stem cells at the level of the basal membrane of the esophageal epithelium.

The esophageal epithelium (13) is at the top of FIG. 4A. The bottom of the esophageal epithelium is similar to a wave called the basal membrane (14) that carries cells called adult stem cells (see element 15 of FIG. 4B) that play an essential role in repairing the esophageal epithelium if the wall is injured by disease or in our case by esophageal resection as in biopsies of the esophagus or deeper resections such as endoscopic mucosal resection (EMR) or endoscopic submucosal resection (ESD). The lamina propria immediately under the basal membrane (16) is part of the mucosa and the muscularis mucosae (19) separates the mucosa from the submucosa (17). The muscularis propria (20) itself has 2 layers with complex nerve systems (not shown). This demonstrates that the esophagus that appears to be a simple tube is in fact a much more complex organ than expected at first sight.

Figure 5:
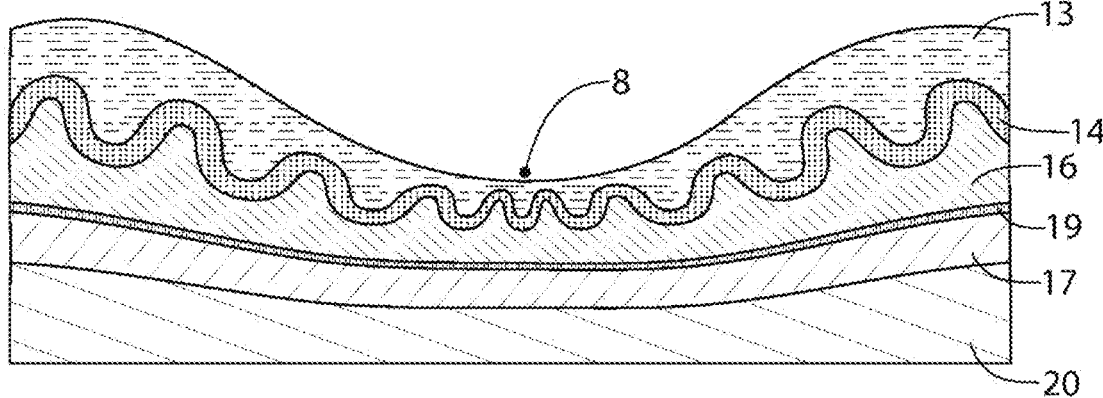
FIG. 5 shows a niche created by the ring of the DM-1 GARD™ compressing the different layers of the esophageal wall.

FIG. 5 illustrates the compression niche (8) left after removal of the DM GARD™ and its thick ring that presses on the esophageal wall as shown in FIG. 1. This niche will facilitate the positioning of the much softer mesh ring of the Therapeutic GARD™. Elements 13, 14, 16, 17, 19, and 20 of FIG. 5 show the different layers of the esophageal wall that have been compressed by the ring of the DM GARD™.

Figure 6:
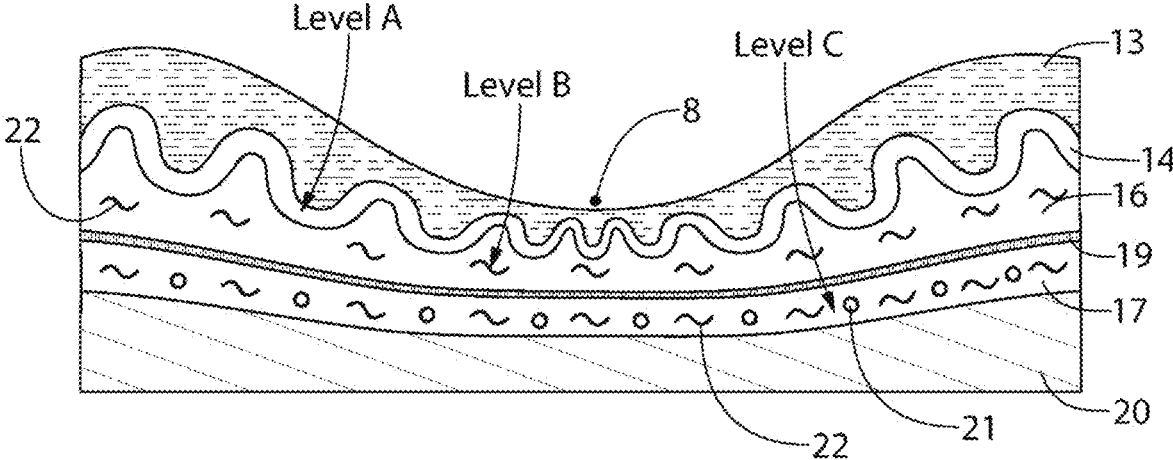
FIG. 6 illustrates different layers of the esophageal wall with the depth of penetration (level) of different methods of endoscopic resection of the esophageal wall.

FIG. 6 illustrates the different depths of esophageal resection that can be used. In most cases, Level A reaching the basal membrane with standard biopsies or level B reaching the lamina propria with endoscopic mucosal resection (EMR) should be sufficient to place the mesh of the Therapeutic GARD™ in position. Level C (submucosa) using Endoscopic submucosal dissection should only be used if longer, heavier tubes such as the OB2-GARD and OB3-GARD are needed to treat obesity since complications of using ESD are not unusual. Fibroblasts (22) from the lamina propria and the submucosa can also be cultured with the epithelial cells and reinjected once the mesh ring has been positioned in place. Blood vessels in the submucosa (21) are also shown. In certain cases, Level A and Level B can be combined by doing EMR and biopsies as well as Level B and Level C by doing EMR and ESD and some standard biopsies can be added.

Figure 7:
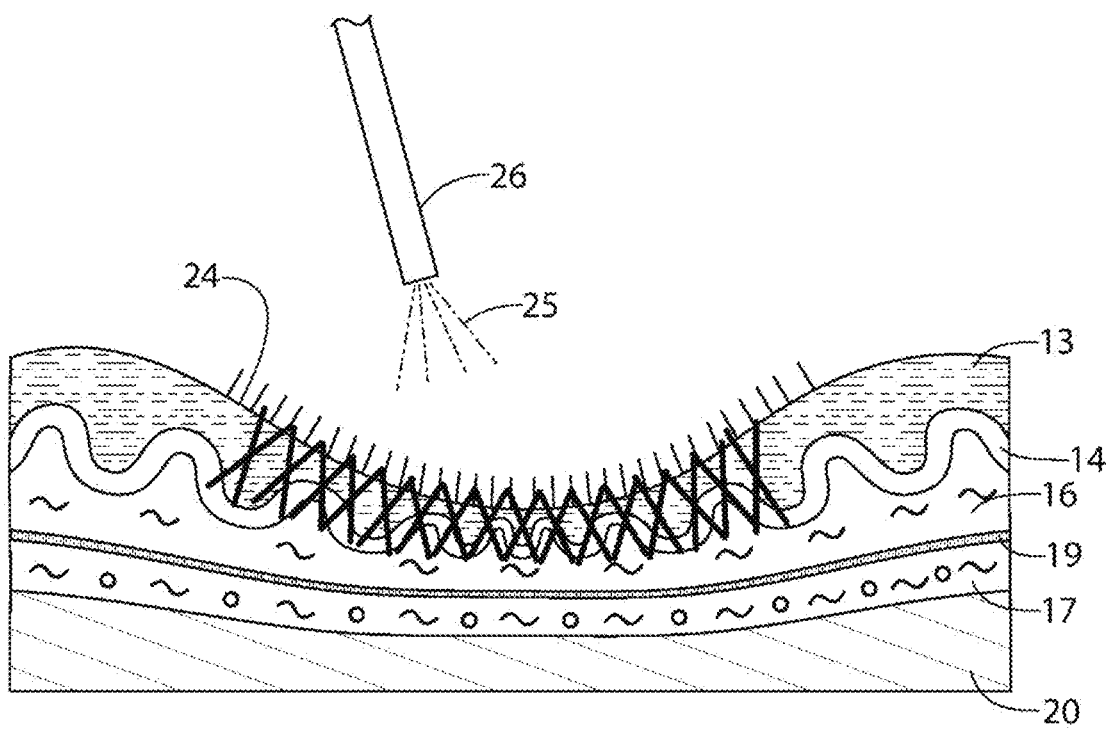
FIG. 7 illustrates that after mucosal resection (X), Platelet Rich Plasma (PRP) with calcium gluconate are sprayed on the bottom of the bleeding niche. Resected mucosa (X) including stems cells is kept for later reinjection (not shown)

FIG. 7 symbolizes the partial resection of the wall of the esophagus with biopsies and/or EMR (24) and the bleeding (PRP) prepared at the beginning of the procedure with Calcium gluconate to make the PRP more viscous is sprayed (25) with a spray catheter (26) passed through the gastroscope (not shown)

Figure 8A:
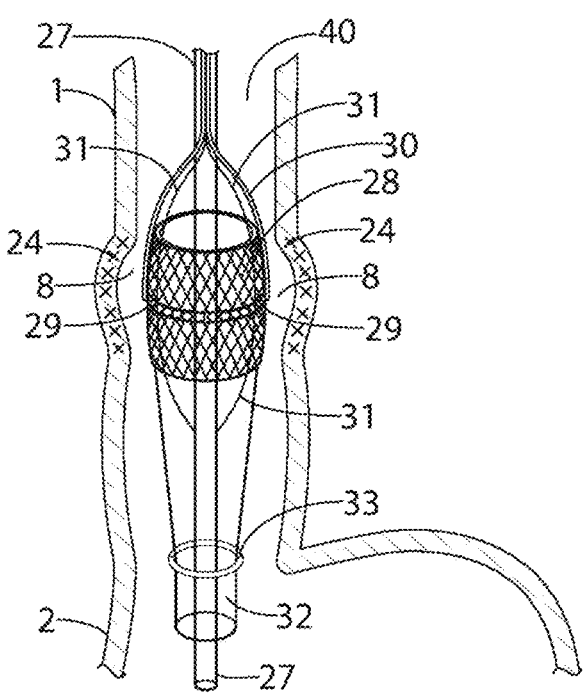
FIG. 8A illustrates one embodiment of the presently disclosed technology where a delivery catheter with a balloon that is used to deploy the mesh ring held on the delivery catheter with a stretchable magnetic bead ring.

In FIG. 8A, the mesh ring (28) of the Therapeutic GARD™, here the GARD™ for GERD in its tubular form, is passed folded on the balloon (31) of a delivery catheter (27) through the mouth and into the esophagus and kept in place with a stretchable ring of magnetic beads (29). The tube of the GARD™ for GERD is also folded on the delivery catheter with a slip knot (33). The mesh is placed facing the bleeding niche (8) under endoscopic vision. Element 24 in FIG. 7 is the sites of the biopsies where viscous PRP has been sprayed. FIG. 8A shows the lumen (40) of the esophagus.

Figure 8B:
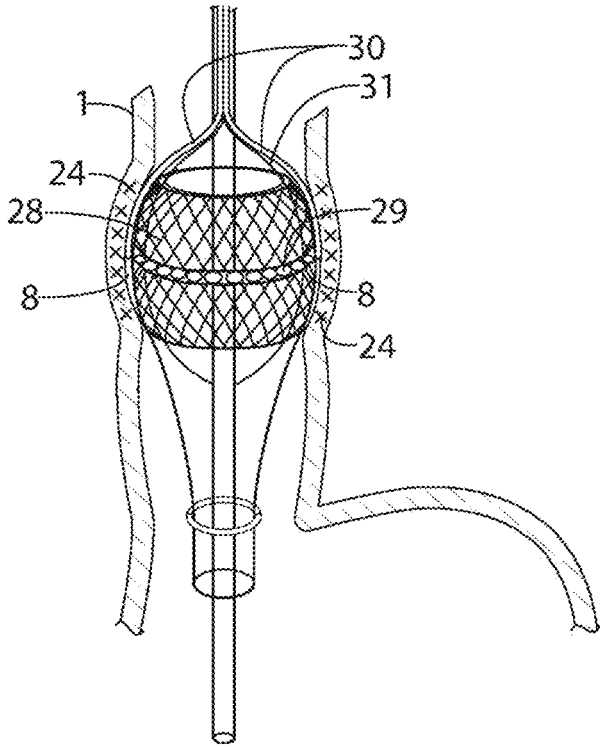
FIG. 8B shows the inflated balloon pressing the mesh ring on the bleeding niche where PRP and calcium gluconate were sprayed to integrate the mesh ring in the coagulating blood.

FIG. 8B illustrates the balloon (31) that is inflated and the mesh ring is held in position with the stretched ring of magnetic beads (29) that presses the mesh ring on the niche (8), where the mucosal biopsies have been made and the PRP with calcium gluconate have been added (see FIG. 7).

The 2 strings holding the magnetic bead ring (29) are loose. The tubular part of the GARD for GERD device (32) is held folded on the delivery (27) with the slip knot.

Figure 8C:
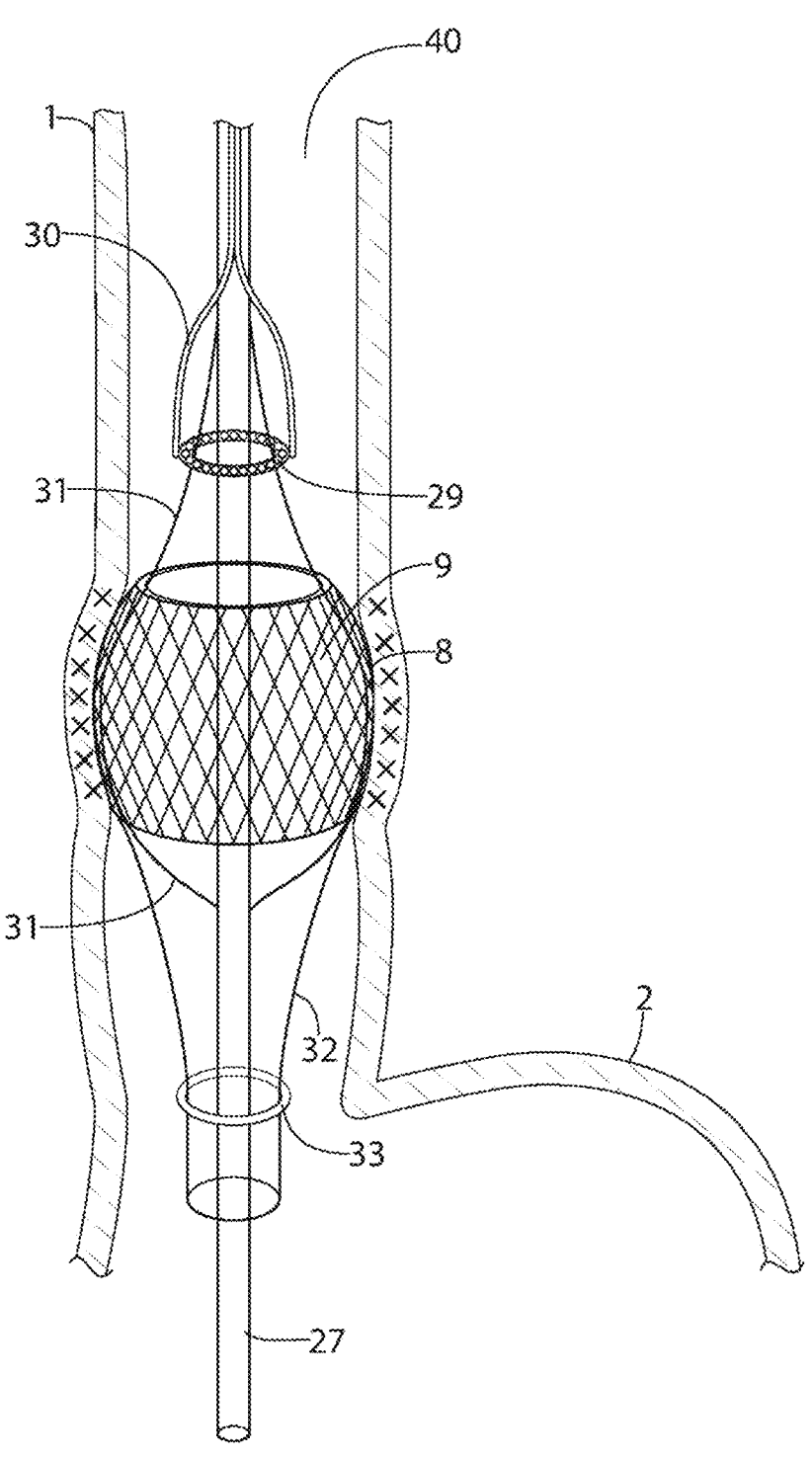
FIG. 8C shows the magnetic bead ring that has been removed by pulling on threads and the net ring is pressed with the balloon against the wall of the niche. The slip knot on the tube is still in place and holds the GARD™ for GERD device allowing removal of the magnetic beads while keeping the position of the device.

As shown in FIG. 8C, the magnetic bead ring (29) has been pulled from the mesh ring (9) by pulling on the other end of the threads (30) at the head of the delivery catheter (not shown). This allows the inflated balloon (31) on the delivery catheter (27) to compress the mesh ring (9) on the niche with the coagulating blood and the added PRP with gluconate calcium (see FIG. 7). FIG. 8C shows the lumen (40) of the esophagus.

Figure 9A:
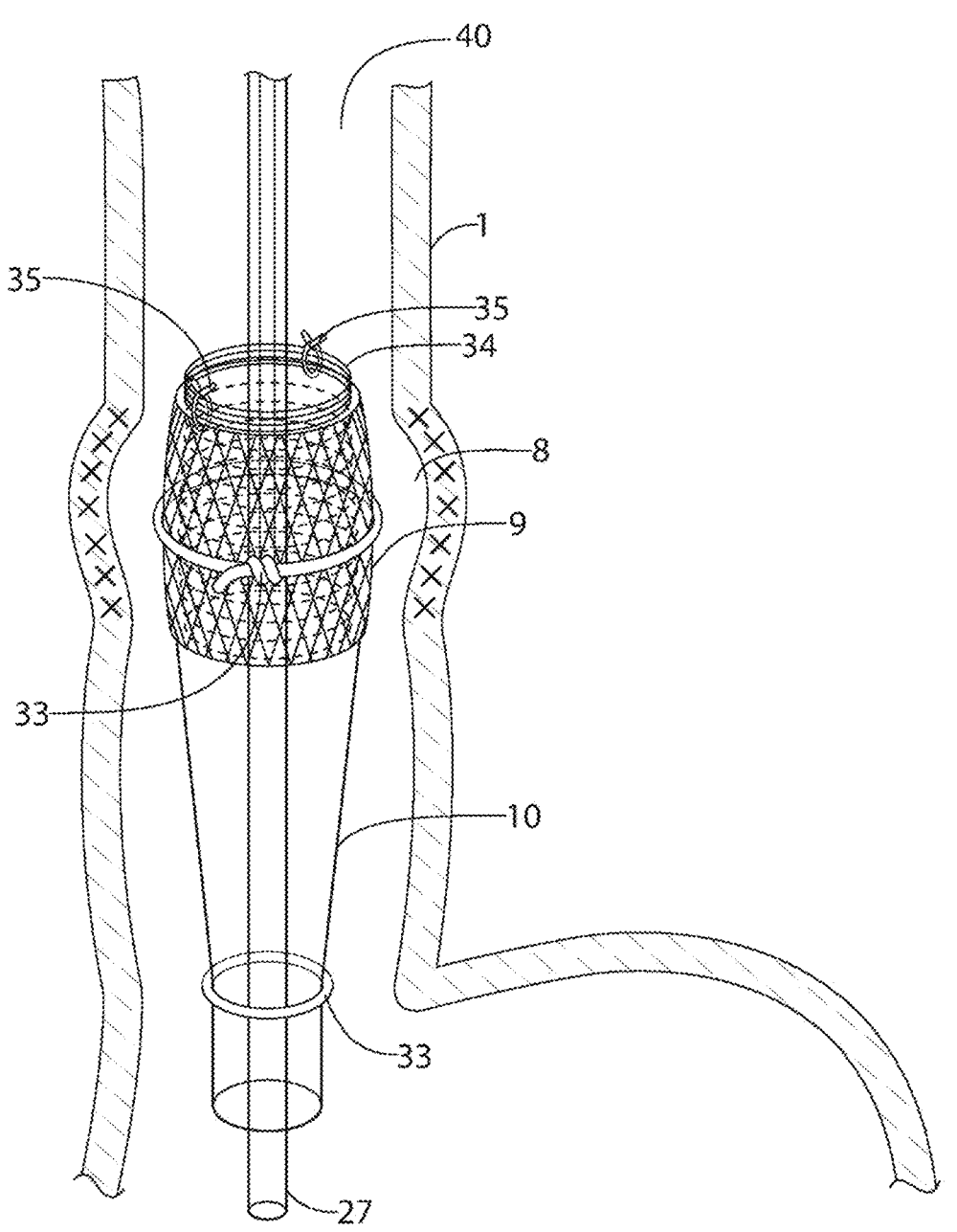
FIG. 9A illustrates one embodiment of the presently disclosed technology, wherein instead of a balloon, a helical spring ring is placed inside the mesh ring and folded on the delivery, similarly to the introduction of the DM GARD™. Knots are holding the mesh ring on the helical spring to avoid any displacement of the mesh ring when the slip knots are pulled out and the helical spring is deployed.
Figure 9B:
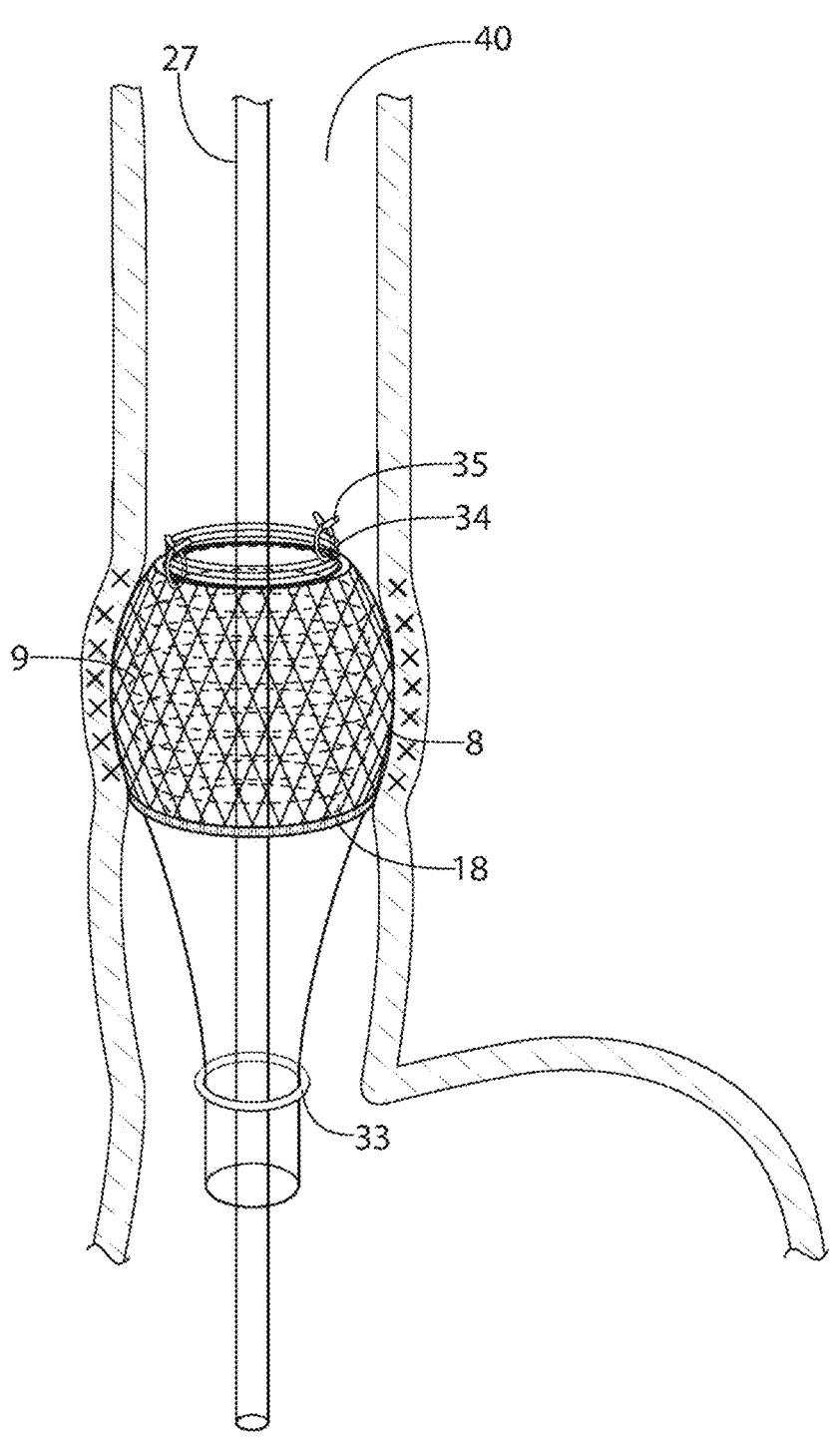
FIG. 9B illustrates that the surgical threads holding the mesh ring will be cut or pulled endoscopically once the helical spring is deployed and the mesh ring is in contact with the patient's blood, PRP and calcium gluconate in the bottom of the niche.

According to another embodiment of the presently disclosed technology, FIG. 9A illustrates a method of placement of the GARD™ for GERD on the niche (8) using a free helical pressure ring (34) similar to the ring of the DM-GARD (7) in FIG. 1 placed inside the mesh ring (9) that is folded and held In position on the delivery catheter (27) with a slip knot (33). When in position facing the bleeding niche (8), the slip knot is pulled. FIG. 9B shows the lumen (40) of the esophagus. The delivery catheter also has a balloon (31) placed on the delivery catheter.

FIG. 9B illustrates the GARD™ for GERD deployed with the helical pressure ring (34) exerting pressure on the mesh ring (9) on the niche (8). One or more knots (35) can hold the mesh ring (9) on the helical ring or spring (34) (e.g., the helical ring can contain or comprise a nitinol helical spring). Each knot (35) can be a slip knot that can be easily pulled out or a regular knot that have to be cut with a scissor through the endoscope (not shown). FIG. 9B shows the lumen (40) of the esophagus.

Figure 9C:
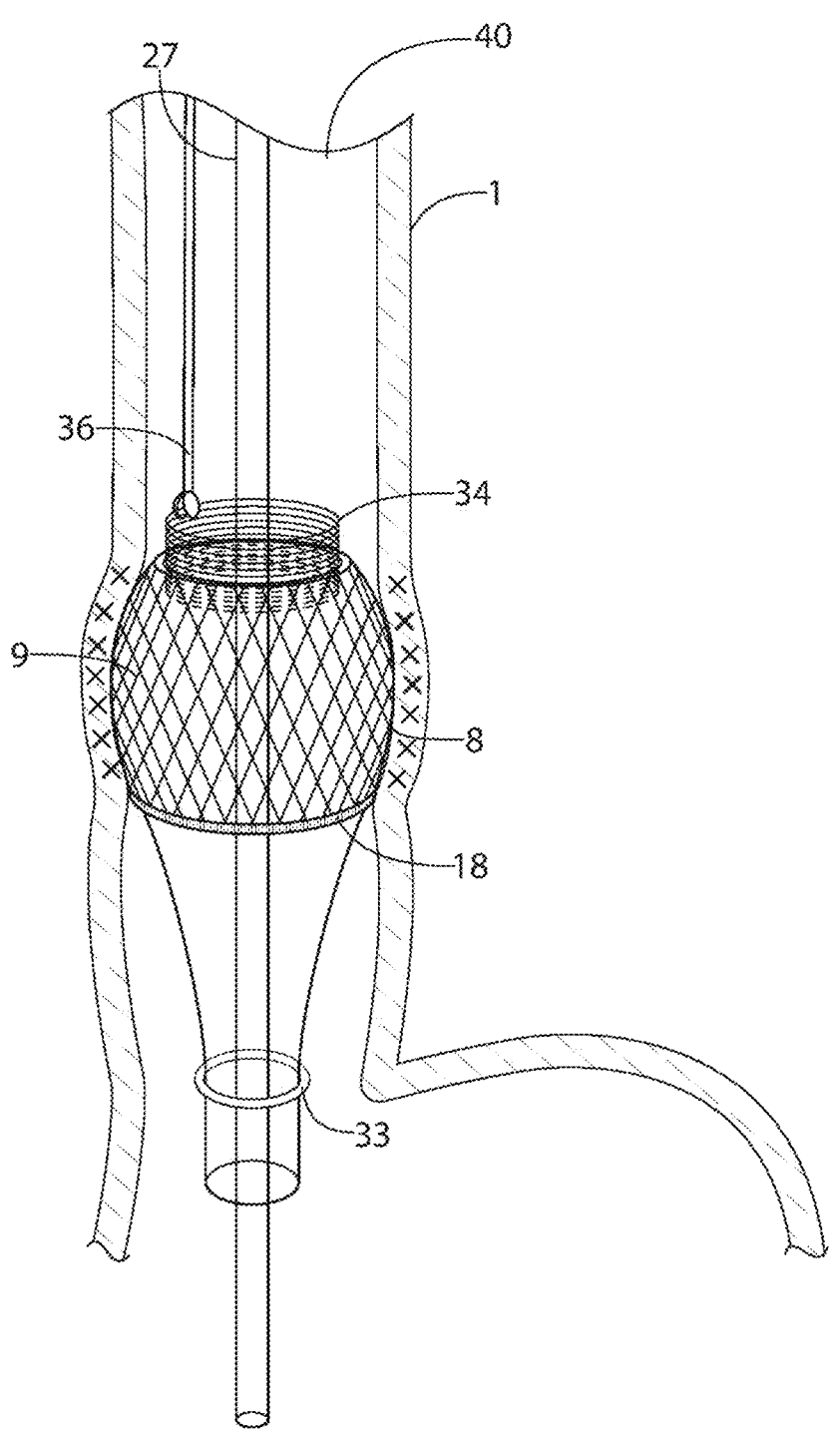
FIG. 9C illustrates that the helical spring is delicately removed and pulled out leaving the mesh ring in place in contact with the coagulating mixture in the bottom of the niche.

FIG. 9C illustrates that the knots (35) have been removed and the helical spring is gently pulled out with a forceps (36) leaving the mesh ring (9) positioned on the niche (8) where biopsies have been taken (x) and the coagulating blood with viscous PRP and calcium gluconate have been added (see FIG. 7). The slip knot (33) holding the tubular part of the GARD™ for GERD is still in position to exert a counterforce to the traction on the helical spring. FIG. 9C shows the lumen (40) of the esophagus.

Figure 9D:
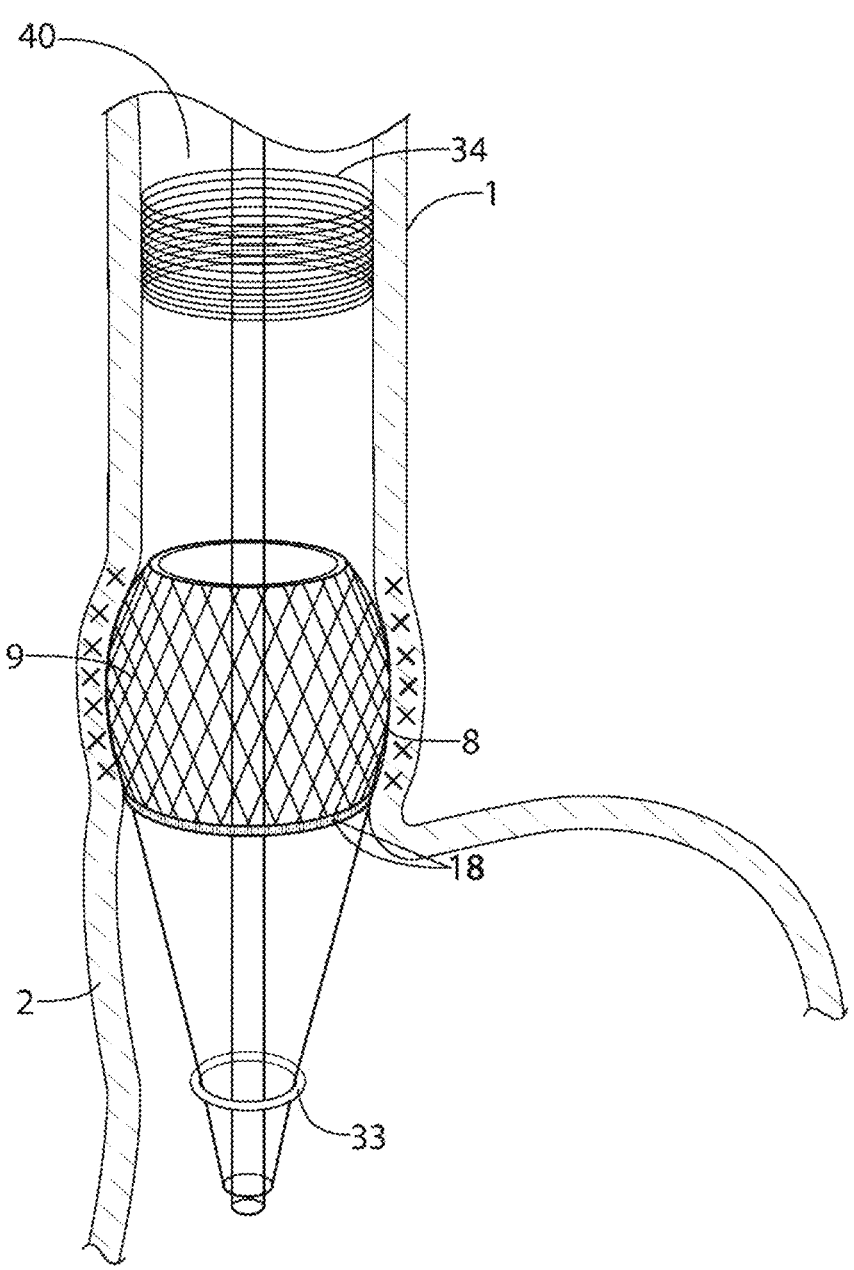
FIG. 9D illustrates that the mesh ring is free in the bleeding niche with PRP and gluconate calcium. The slip knot holding the tubular part of the GARD™ for GERD is still in position to maintain device in place.

FIG. 9D illustrates the mesh ring (9) is in position and the delivery catheter (27) is still kept in place holding the tubular valve with the slip knot. FIG. 9D shows the lumen (40) of the esophagus. The removable helical spring (34) has been pulled back towards the top of the esophagus to free access to the "inner" or luminal side of the mesh ring (9). The balloon (31) is not inflated and the slip knot (33) on the tubular part of the delivery is still in position.

Figure 10A:
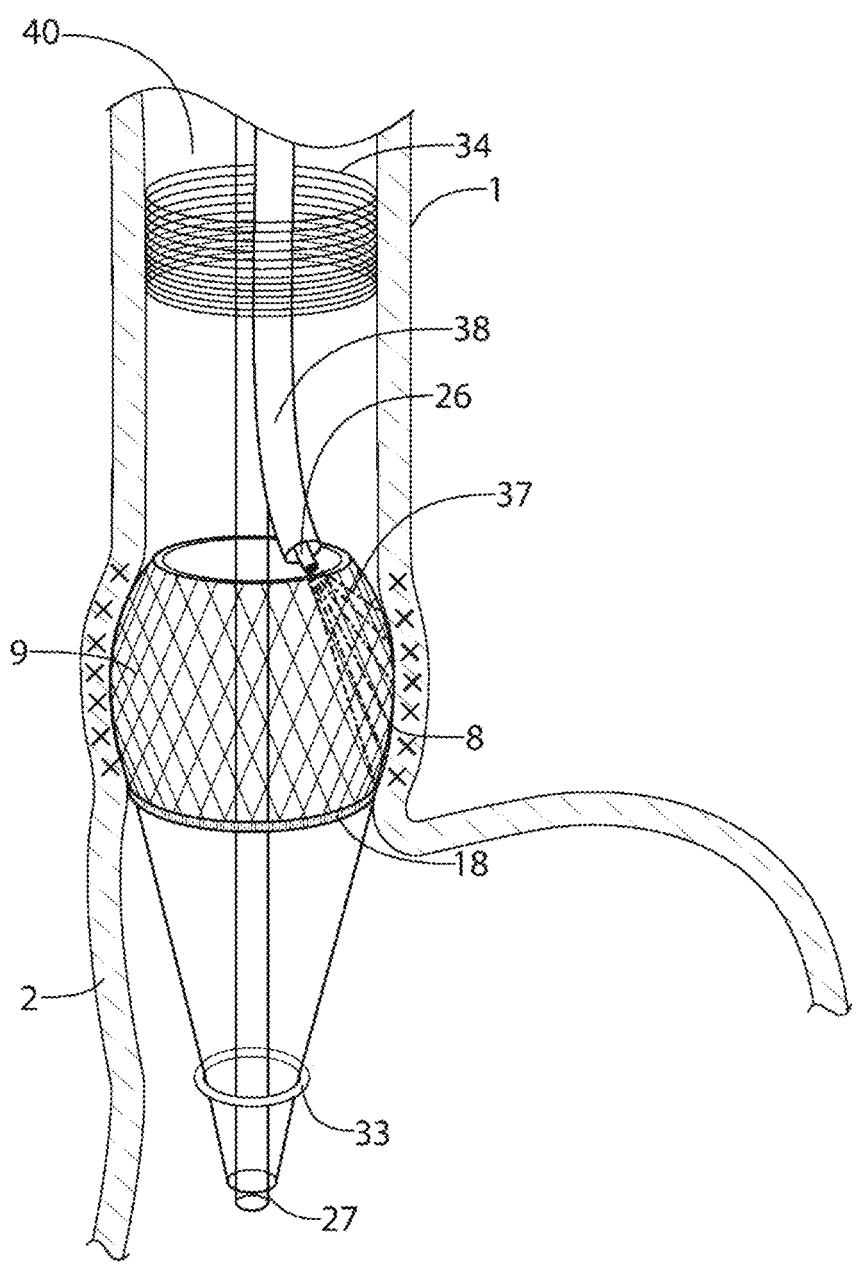
FIG. 10A illustrates that fragments of the biopsies of the epithelium cells obtained in the beginning of the procedure with or without cultured epithelial cells obtained when the DM GARD™ was placed originally are sprayed in a PRP/calcium gluconate solution on the "luminal" side of the mesh to reconstitute the esophageal epithelium.

FIG. 10A illustrates that the mesh ring (9) is sprayed through the endoscope (38) with epithelial cells that have been placed in culture when the DM-GARD was first positioned in the esophagus and/or fragments of the biopsies of the esophageal wall containing adult stem cells of the epithelium of the esophageal wall cut up after biopsies were taken in the bottom of the niche (see FIG. 9) at the beginning of the procedure placing the Therapeutic GARD devices in the esophagus. In FIG. 10A, a balloon (31) that is fixed or otherwise secured on the delivery catheter is shown as not yet inflated.

The slip knot (33) of the tube is still in place and the delivery catheter (27) is in position. The helical spring (34) has been pulled upwards and the endoscope (38) passes through the helical spring to spray the luminal side of the mesh ring (9) with epithelial cells in PRP with calcium gluconate (37) to make the mixture more viscous and adhering to the mesh ring (9) so as to reconstitute the epithelial layer of the esophageal wall.

Figure 10B:
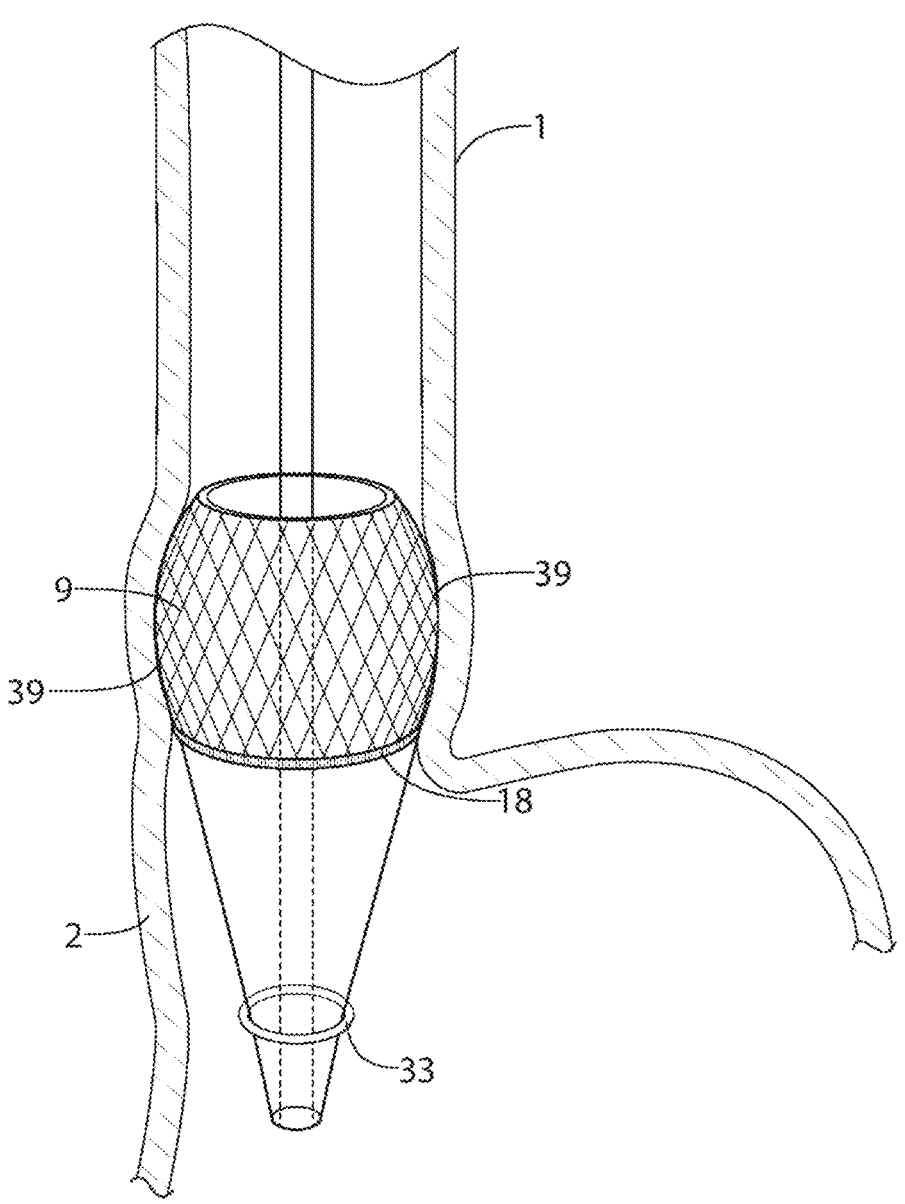
FIG. 10B illustrates that the mesh ring is now "sandwiched" between the bottom of the coagulating niche and the reconstituted autologous epithelium of the esophageal wall

FIG. 10B illustrates the inflated balloon (31) on the delivery catheter pressing outwardly on the epithelial cells that were just sprayed on the mesh ring (9) so that the mesh ring (9) is "sandwiched" between the "external" niche containing coagulating blood and PRP/calcium gluconate and the "internal" reconstitution of the epithelial layer after spraying the adult stem cells in PRP to regenerate the epithelial layer in vivo.

Figure 11A:
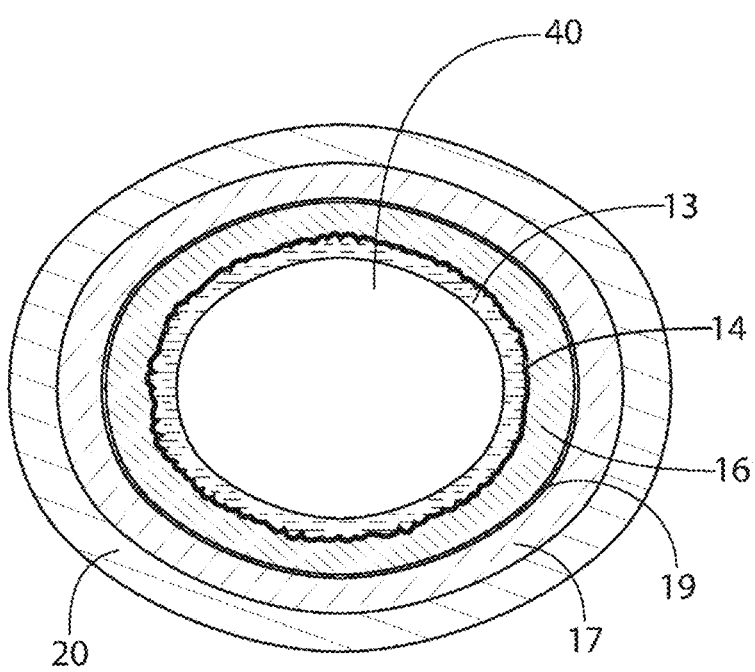
FIG. 11A shows the different layers of the normal esophageal wall.

FIG. 11A illustrates a transverse view of the esophagus as shown in a longitudinal view in FIG. 6A. Visible in FIG. 11A is the esophageal epithelium (13), the basal epithelium (14), the lamina propria (16), the muscularis mucosae (19) separating the mucosal part (13, 14, 16) from the submucosa (17) and the muscularis propria (20). FIG. 11A shows the lumen (40) of the esophagus.

Figure 11B:
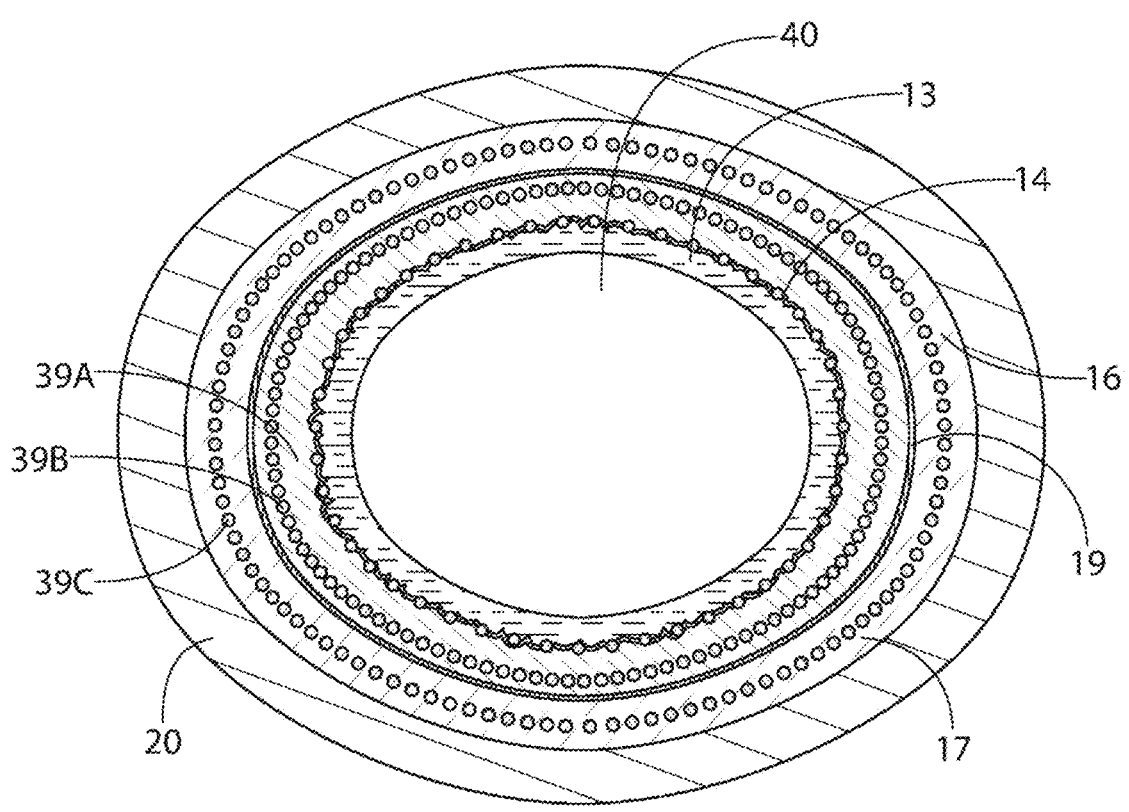
FIG. 11B illustrates the different depths of placement of the mesh ring depending how deep the mucosal resections are according to one embodiment of the present disclosed technology.

FIG. 11B illustrates various options for the depth of placement of the mesh ring in the esophageal wall at the end of the procedure. Location (39A) is the most superficial placement of the mesh ring at the level of the basal epithelium (Level A of FIG. 6). Location (39B) is the mid-level placement of the mesh ring in the lamina propria (16) of the mucosal wall (Level B of FIG. 6). Location (39C) is the deepest placement of the mesh ring in the submucosa (17) (Level C of FIG. 6).

Figure 12:
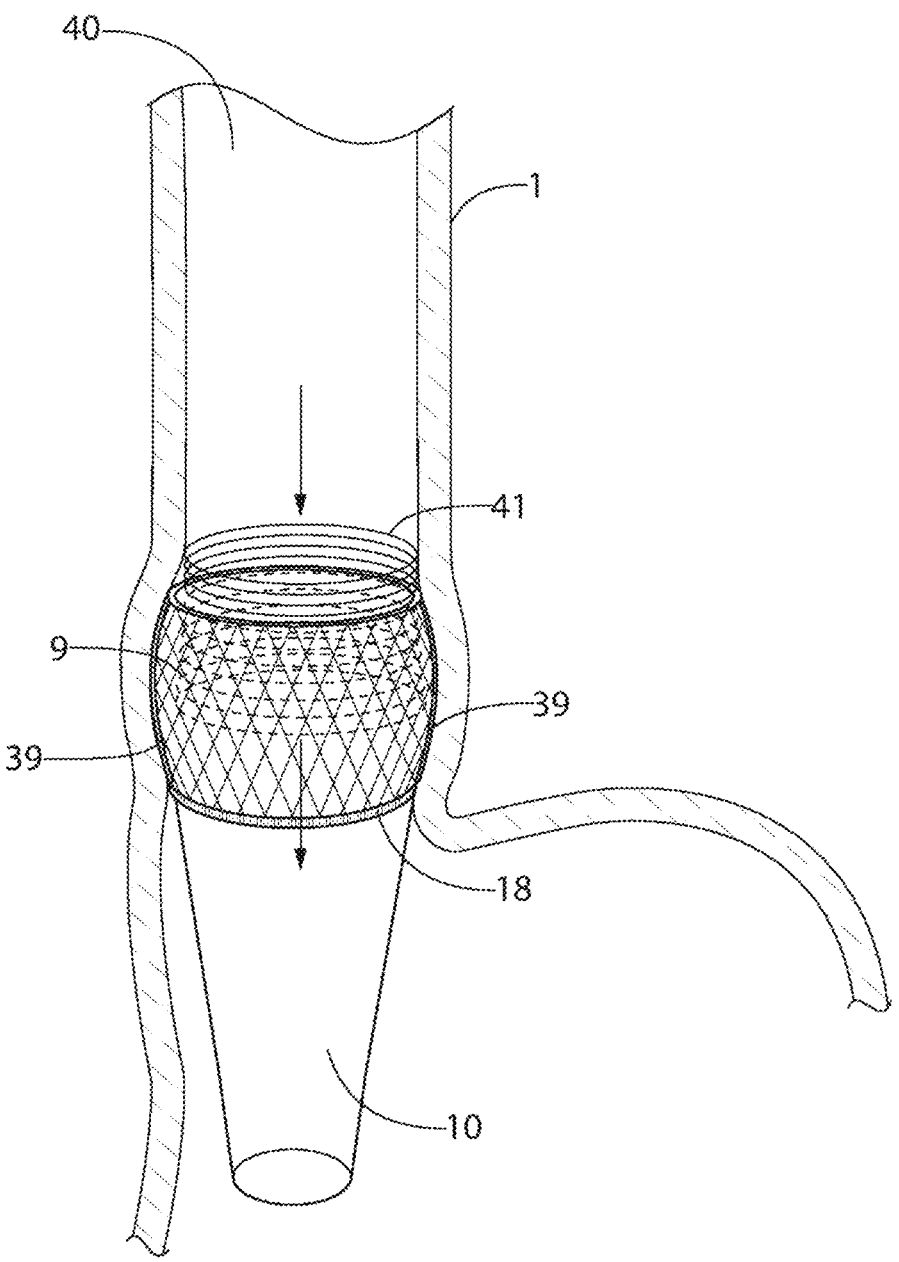
FIG. 12 illustrated a ring of one embodiment of the presently disclosed technology that is used at the end of the procedure to compress the area once the mesh has been covered with epithelial cells and the ring is left in position for a period of time before possible removal. All other remaining devices have been removed from the esophagus. The slip knot is removed on the tube and the tube opens.

FIG. 12 illustrates a final compression ring (41) that is introduced to put pressure on the "reconstituted" esophageal wall after placement of the mesh ring (9) shown integrated in the esophageal wall (39) supporting the tubular or conical valve (10) of the Therapeutic GARDs™ within the esophageal lumen (40). FIG. 12 shows the esophagus (1) and the radio-opaque zone (18) of the Therapeutic GARD that allows location of the Therapeutic GARD after the compression ring with its nitinol radio-opaque springs is removed.

Figure 13A:
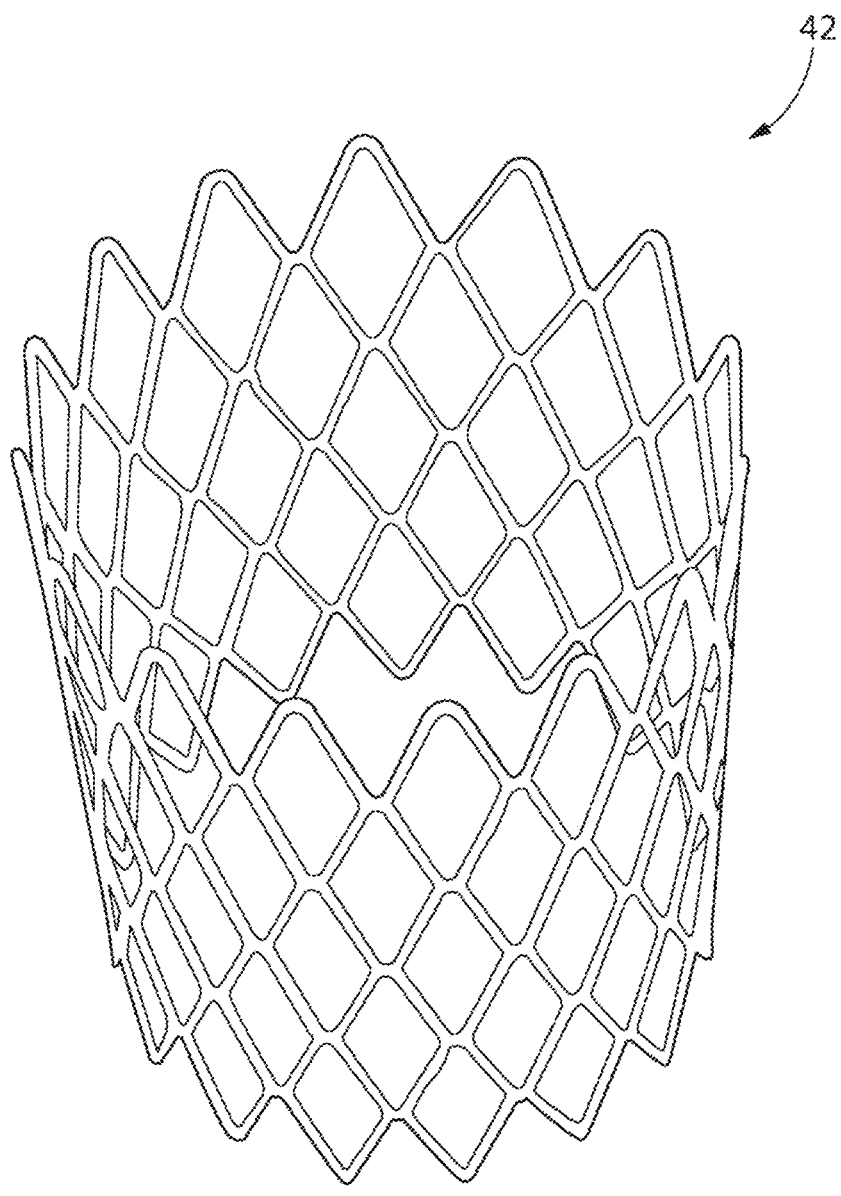
FIG. 13A is a top perspective view of a stent or ring of one embodiment of the presently disclosed technology.
Figure 13B:
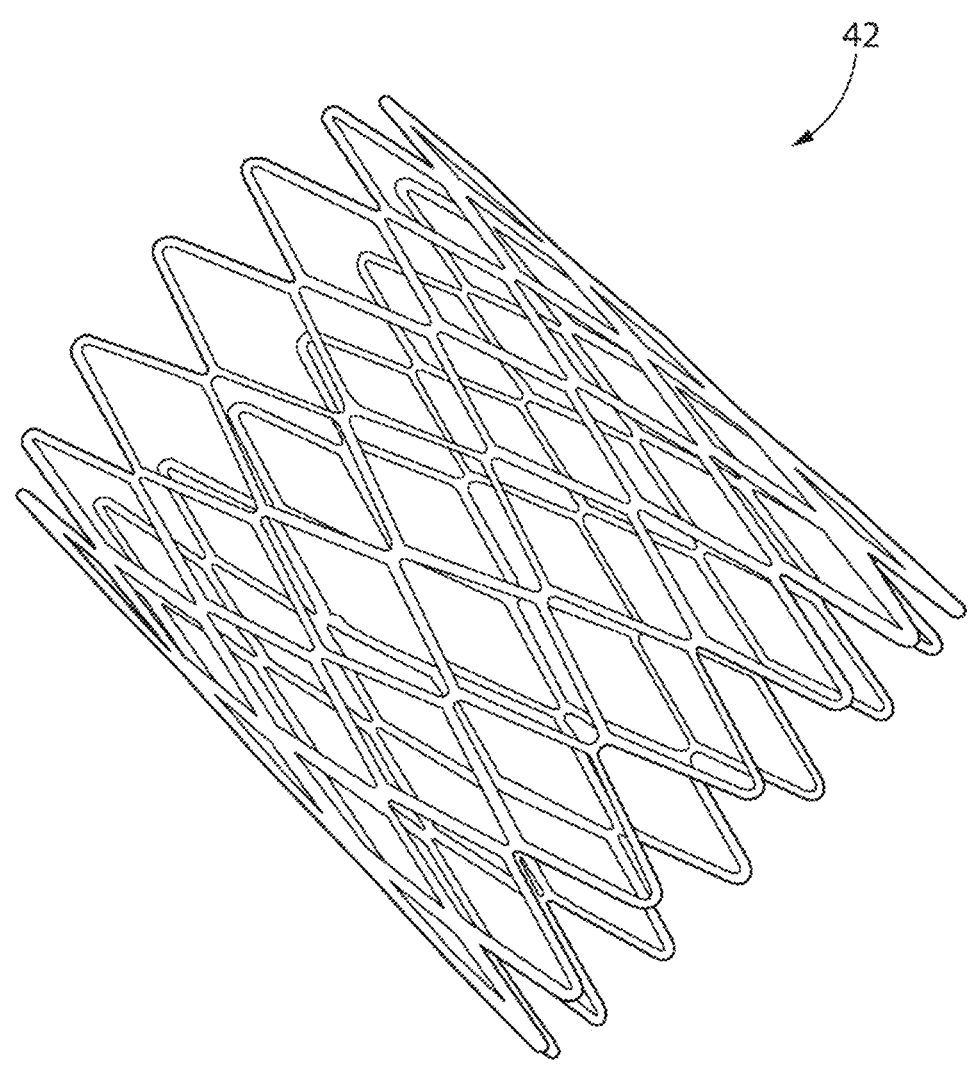
FIG. 13B is a side perspective view of the device shown in FIG. 13A.
Figure 13C:
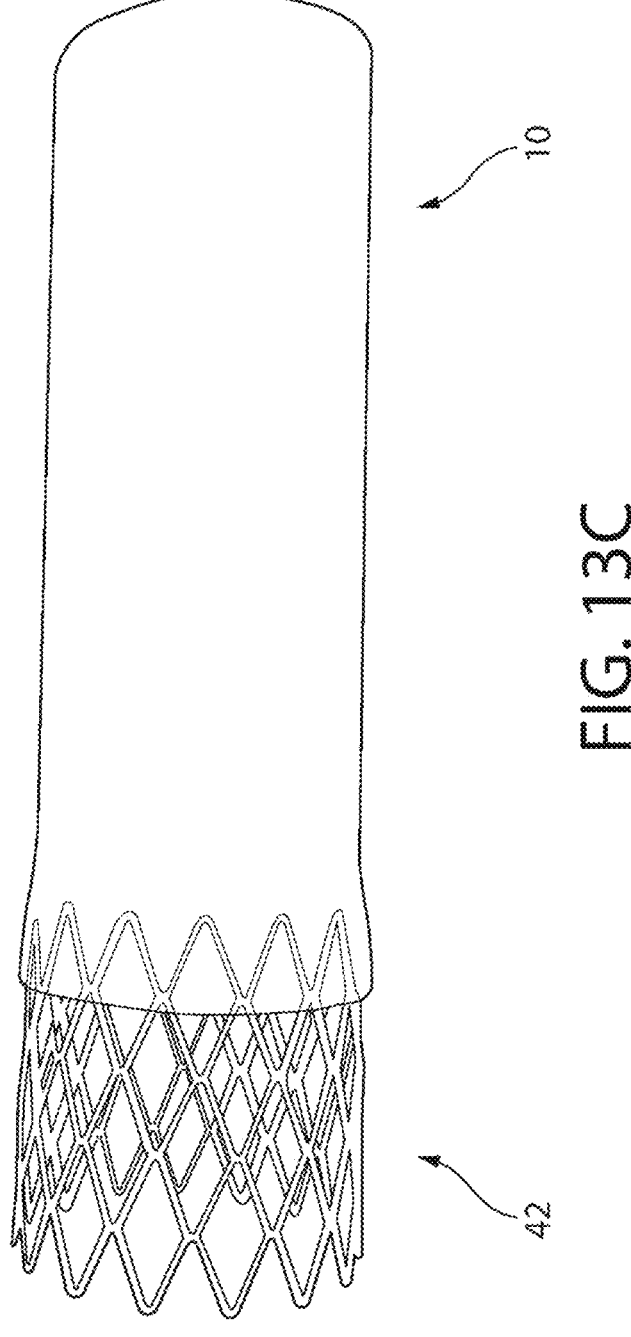
FIG. 13C is a perspective view of the device shown in FIG. 13A attached to a tubular part.

FIGS. 13A-13C show one embodiment of the presently disclosed technology that includes a circular ring 42, optionally formed of nitinol. In one embodiment, the ring 42 is molded in silicone and the DM GARD™ is put in place only temporarily to prepare the esophageal wall for placement of the Therapeutic GARD. In this embodiment, the ring 42 can optionally be removed after a predetermined period of time, such as but not limited to 1 to 4 weeks. In another embodiment of the presently disclosed technology, the ring 42 is not molded in silicone. As a result, in this embodiment, the ring 42 can be permanently integrated into by the esophageal wall.

An advantage of using the nitinol ring 42 is that when the healthcare professional pulls on the strings of the delivery catheter, the ring 42 springs into place. As a result, the ring 42 is placed on the bleeding site caused by the biopsies made just previously. This helps direct the adult stem cells of the esophagus that are injected in the Platelet rich plasma (PRP) solution on the lumenal side of the esophagus, thereby covering the nitinol ring 42 with cells that should reconstitute the normal internal wall (mucosa) of the esophagus. Other materials that have the same desirable properties as nitinol could be used to form the ring 42.

In another embodiment, the ring 42 can be formed of a polymeric material.

Until the presently disclosed technology was developed, healthcare professionals had not been able to place stents (nitinol or plastic) in the esophagus if there was no narrowing of the esophagus. The presently disclosed technology provides this benefit. In addition, previously healthcare professionals had not been able to hold a device in the lumen for therapeutic purposes, which the presently disclosed technology accomplishes.

Thus, in one embodiment the presently disclosed technology includes a combination of a niche created by the DM-GARD™ that is first placed in the esophagus and puts pressure on the wall of the esophagus creating a kind of bedding for the Therapeutic GARD™ (then the DM-GARD™ is removed). In addition, bleeding made by endoscopic biopsies and therefore coagulation after the bleeding helps hold the nitinol ring that support the anti-reflux and/or anti-obesity devices in the lumen of the esophagus and stomach. Furthermore, the presently disclosed technology can include putting the esophageal adult stem cells from the patient obtained by the biopsies in PRP was found to be a good milieu to put cells in culture or repair tissues (but not described to hold a foreign device like the Therapeutic GARD™ in position) and is used to reconstitute and/or repair) the internal mucosa of the esophagus in vivo after damaging it with the biopsies. The above allows for the integration of the stent in the esophageal wall at the mucosal-submucosal level of the esophageal wall and allows holding the anti-reflux and/or the anti-obesity devices in the lumen opening. This creates a completely new era of endoscopic treatment (without surgery) of these very common diseases on an ambulatory basis.

In one embodiment, injection of botulinum toxin will paralyze locally for a few weeks the peristaltic contraction and help the biological sealing of the nitinol ring that is thin (in the order of 0.3 mm thick) in the wall of the esophagus.

Optionally, the nitinol ring is thin, such as in the order of 0.3 mm think. When combined with the muscular layer, the two are about 3 mm thick, at most.

In one embodiment, a method of the presently disclosed technology can include first calibrating the diameter of the esophagus at the level of the esophagus (e.g., lower third) where the healthcare professional intends to put the Therapeutic GARD. Next, the healthcare professional can place the DM-1 GARD™ in and/or at the level identified above for approximately 1-2 weeks to create a niche (e.g., see FIG. 5). Eventually, an experienced healthcare professional could optionally skip this stage to avoid an additional endoscopy. Third, the method can include preparing the PRP from the patient's blood by spinning the blood twice. Fourth, the DM GARD™ is removed from the esophagus. Fifth, at least one and up to twelve biopsies can be taken from the bottom of the niche. For example, ten biopsies can be used for their stem cells and two biopsies can be used to have regular pathology to make sure the basal membrane is present as the adult esophageal stem cells are known to be right at the level of the basal membrane. This can be done for the control of the quality of the biopsies so they include stem cells.

The sixth step of the above-identified embodiment can include placing the biopsies (e.g., possibly cut-up in 2-3 pieces) in the PRP solution. Seventh, the nitinol stent of the Therapeutic GARD™ can be placed on the bleeding niche. Eighth, the PRP with esophageal adult stem cells can be injected on the internal (lumenal) side of the nitinol stent. Ninth, the PRP and stem cells can be compressed on the nitinol stent, such as with a balloon. An optional tenth step can include injecting botulinum toxin above the ring of the Therapeutic GARD™. An optional eleventh step can include positioning an additional helical spring ring on the nitinol stent for additional compression, such as for 1-2 weeks.

In another embodiment, a method of the presently disclosed technology can include, first, balloon calibration. Second, the DM-1 device can be placed at the desired site for a predetermined period of time (e.g., 1 week), thereby creating a niche. Third, the DM-1 device can be removed, and biopsies can be made at the bottom of the niche to obtain adult stem cells. Four, the biopsies can be kept in the PRP obtained from the host (e.g., minipigs or patients). Fifth, the nitinol stent (DM-2 or Therapeutic GARD) can be placed on the bleeding site with the ring part in the bleeding niche. Optionally, lamellar devices can be used. Sixth, the PRP with the biopsies that include adult stem cells can be injected or sprayed on the luminal side of the ring to reconstitute the esophageal wall and incorporate the nitinol ring in the esophageal wall. Seventh, the DM-3 compression ring can be placed on the site for a predetermined amount of time (e.g., a week). Eight, the DM-3 ring can be removed after a predetermined amount of time (e.g., a week). Optionally, some PRP can be added and compressed with a balloon for a predetermined amount of time (e.g., 5-10 minutes). Once the balloon is removed, the procedure is finished.

The following exemplary embodiments further describe optional aspects of the presently disclosed technology and are part of this Detailed Description. These exemplary embodiments are set forth in a format substantially akin to claims (each set including a numerical designation followed by a letter (e.g., "A," "B," etc.), although they are not technically claims of the present application. The following exemplary embodiments refer to each other in dependent relationships as "embodiments" instead of "claims."

1A. A method for maintaining a medical device in place in a lumen of a hollow organ of a patient for a period of months or years without using a metal or bioresorbable stent.

1B. A method for placement of a medical device in a lumen of the gastrointestinal tract of a patient using a flexible endoscope having at least one 2.8 mm working channel for placement of a guidewire, biopsy forceps, endoscopic mucosal resection or endoscopic submucosal dissection devices as well as injection and spraying devices and aspiration of fluids and aspiration of air or blood or secretions.

1C. A method for placement of a permanent medical device in a wall of an esophagus of a patient using a first short-term device that is similar to a final device but without incorporation in the wall of the esophagus to evaluate safety and efficacy of the final device before permanent placement in the wall of the esophagus of the final device.

1D. A temporary device using essentially pressure on a wall of a lumen of an esophagus after calibration of a size of the esophagus that can be easily removed through the mouth after a period of one day to 1 month, usually 2 to 3 weeks.

1E. A temporary device with a thick ring leaving a niche on an esophageal wall once removed that is used to place a soft mesh ring of one of long-term Therapeutic-GARDs.

1F. A method for placement of medical devices using mucosal resection with standard biopsies or larger and deeper pieces of an esophageal wall using endoscopic mucosal resection (EMR) or endoscopic submucosal dissection (ESD) removing esophageal mucosa and having the wall of the esophagus bleed, then spraying plasma rich platelet solution obtained from the patient's blood prior to placement of the devices to help a longer-term device incorporate within to the esophageal wall.

1G. A method of isolating a portion of the esophagus to place temporary or permanent medical devices in a wall of the esophagus using biopsies to make the wall of the esophagus bleed adding platelet rich plasma to help adhesion and incorporation of medical devices in the esophageal wall made with an incorporated upper mesh ring and tubular devices placed in the luminal wall to treat at least one of Gastroesophageal reflux disease (GERD) or obesity.

1H. A method of isolating a portion of an esophagus of a patient to place temporary or permanent medical devices in a wall of an esophagus using local injection of botulinum toxin to decrease peristaltic contraction of the esophagus for a few weeks or months to keep the device in place to help a permanent device stay in position.

1I. A temporary device leaving a pressure niche on a wall of an esophagus of a patient that will be used to place longer term devices for treatment of at least one of Gastroesophageal Reflux Disease (GERD) or excess body weight.

1J. A method of using a combination of biopsies of an esophageal epithelium to obtain esophageal cells for culture and reinjection at a later endoscopy or immediately for repairing the esophageal epithelium resected to place a net or mesh ring within a wall of esophagus.

1K. A method of using culture of esophageal cells for reinjection at a later endoscopy or immediate reinjection of esophageal cells in platelet rich plasma (PRP) with calcium gluconate as a culture medium in vivo for repairing esophageal epithelium resected to contain a net or mesh ring in a wall of an esophagus of a patient that supports medical devices in a lumen of the esophagus.

1L. A method of using bleeding and injection of autologous platelet rich plasma (PRP) solution in an esophagus of a patient to help heal lesions caused by mucosal resection to obtain epithelial cells for culture or incorporation of a mesh net ring in a esophageal wall.

1M. A method of using platelet rich plasma with small fragments of about 1 mm of epithelial mucosa to culture an epithelium on a luminal side of a mesh ring so as to repair the epithelium and help incorporate safely the mesh ring at a flexible endoscopy to support luminal devices.

1N. A method of using platelet rich plasma with small fragments of epithelial mucosa to culture an epithelium on a luminal side of a mesh ring so as to repair the epithelium and help incorporate safely the mesh ring at a flexible endoscopy to support luminal devices to treat gastroesophageal reflux.

1O. A method of using platelet rich plasma with small fragments of epithelial mucosa to culture an epithelium on an external side (submucosal and muscular side of the esophagus) of a mesh ring so as to repair a wall and help incorporate safely the mesh ring using cultures of epithelial cells or culture of fibroblasts from a lamina propria obtained at flexible endoscopy to support luminal devices.

1P. A method of using platelet rich plasma with small fragments of epithelial mucosa to culture a epithelium on a luminal side of a mesh ring so as to repair the epithelium and help incorporate safely the mesh ring at flexible endoscopy to support luminal devices to treat gastroesophageal reflux blocking reflux yet allowing vomiting (lamellar device).

1Q. A method of using platelet rich plasma with small fragments of epithelial mucosa to culture an epithelium on a luminal side of a mesh ring so as to repair a epithelium and help incorporate safely the mesh ring at flexible endoscopy to support luminal devices to treat obesity.

1R. A method of culturing esophageal cells in vitro obtained from biopsies at a time of placement of the temporary device to supplement the endogenous culture of epithelial cells if needed at the time of the second definitive device for treatment of gastroesophageal reflux or obesity.

1S. A helical ring used to deploy a soft mesh ring of a definitive device, help place the mesh ring in position and exert pressure on the mesh ring so as to pressure the mesh in position on the bleeding, coagulating mix of blood, PRP and calcium gluconate.

1T. A delivery catheter using a helical spring to put pressure on an esophageal wall side of a mesh in a niche and help the mesh adhere to a mix of blood, PRP and gluconate calcium in the niche and a balloon on a delivery to press on the luminal epithelial cell layer after epithelial cells with PRP have been sprayed on the mesh to help sandwich the mesh in the wall of the esophagus.

1U. A soft mesh ring comprising or consisting of polypropylene, polyester, polyethylene terephthalate (PET), polytetrafluoroethylene (PTFE), polyvinylidene fluoride (PVDF), synthetic compounds integrating animal collagen components, and mixtures thereof, among others.

1V. The use of a delivery device to insert a definitive device and a mesh ring into a patient, the use comprising releasing the definitive device and the mesh ring in position under endoscopic control.

1W. The use of a balloon to introduce a definitive device, the use comprising inflating the mesh net ring in position and exert pressure on the mesh before removing the balloon to allow cultured endogenous or exogenous autologous epithelial cells to be injected to repair and restore original esophageal epithelium.

1X. A mesh ring that is radio-opaque to localize the mesh ring with fluoroscopy without repeating a gastroscopy.

1Y. A glue used to have the mesh of the ring adhere to the tubular part of a Gastro-intestinal Anti-Reflux Device that is radio-opaque by mixing silicon glue with a radio-opaque substance.

1Z. A glue inducing adhesion of a mesh of a ring to a tubular part of a Gastro-intestinal Anti-Reflux Device that is radio-opaque by mixing silicon glue with a radio-opaque substance such as barium sulfate.

1AA. A tubular or lamellar GARD made of a medical grade plastic.

1AB. A tubular or lamellar GARD made of a medical grade implantable silicone.

1AC. A method of allowing integration of a mesh ring using platelet rich plasma (PRP) obtained from a patient's own blood, wherein a mesh ring is integrated within a wall of the patient's esophagus between the PRP added to the biopsy sites of the wall of the esophagus that helps coagulation and grips the mesh on an external side of the mesh ring, wherein esophageal cell wall stem cells that are obtained from biopsies and are reinjected on an internal or luminal side of the mesh ring.

1AD. A method of preventing displacement of a prosthesis, optionally a stent and optionally formed of nitinol, the method comprising:
    inserting the prosthesis into a preexisting passageway of a living organism, the prosthesis contacting an interior wall of the passageway; and
    applying plasma, optionally platelet rich plasma (PRP), to at least one of the wall and the prosthesis so that the prosthesis becomes integrated into the wall of the passageway.

16

1AE. A system comprising:
    a prosthesis, optionally a stent and optionally formed of nitinol, configured to contact or engage an interior wall of a preexisting passageway of a living organism, and
    plasma, optionally platelet rich plasma (PRP), for applying to at least one of the wall and the prosthesis so that the prosthesis becomes integrated into the wall of the passageway.

2AE. The system of embodiment 1AE, wherein the system is configured to prevent displacement of the prosthesis in the passageway.

3AE. The system of embodiment 1AE or 2AE, wherein the plasma is sprayed or injected.

4AE. The system of embodiment 1A, 2AE, or 3AE, wherein the prosthesis is sutured to at least a portion of the passageway.

5AE. The system of embodiment 1A, 2AE, 3AE, or 4AE, wherein the plasma is compressed onto the prosthesis.

While the presently disclosed technology has been described in detail and with reference to specific examples thereof, it will be apparent to one skilled in the art that various changes and modifications can be made therein without departing from the spirit and scope thereof. It is understood, therefore, that the presently disclosed technology is not limited to the particular embodiments disclosed, but it is intended to cover modifications within the spirit and scope of the present presently disclosed technology as defined by the appended claims.

The invention claimed is:

1. A method of minimally-invasive treatment of at least one of reflux disease and obesity of a patient, the method comprising:
    inserting a nitinol stent through a mouth of the patient;
    placing the nitinol stent in at least a portion of an esophageal wall of an esophagus of the patient; and
    applying a platelet rich plasma (PRP) solution of the patient onto at least one of the nitinol stent and the esophageal wall so that the stent becomes integrated into the esophageal wall, the PRP solution including stem cells of the patient.

2. The method of claim 1, further comprising:
    suturing through the esophagus and the nitinol stent to attach the stent securely to the esophageal wall.

3. The method of claim 1, wherein the step of applying includes injecting or spraying.

4. The method of claim 1, wherein the nitinol stent is inserted into the mouth of the patient after a diagnostic device is removed from the esophagus after a predetermined period of time.

5. The method of claim 1, further comprising:
    compressing the PRP onto the nitinol stent.

6. A nitinol stent configured to be placed through a mouth of a patient and in an esophageal wall of an esophagus of the patient, the nitinol stent including a platelet rich plasma (PRP) solution of the patient thereby allowing the nitinol stent to be integrated into the esophageal wall, the PRP solution including stem cells of the patient.

* * * * *